US009750898B2

United States Patent
Davies et al.

(10) Patent No.: US 9,750,898 B2
(45) Date of Patent: Sep. 5, 2017

(54) MEDICATED MODULE WITH INTERLOCK

(75) Inventors: James Alexander Davies, Warwickshire (GB); John David Cross, Northhamptonshire (GB); Malcom Stanley Boyd, Warwickshire (GB); Steven Wimpenny, Warwickshire (GB); Daniel Thomas De Sausmarez Lintell, Warwickshire (GB); Simon Lewis Bilton, Warwickshire (GB); Naceur Rekaya, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1035 days.

(21) Appl. No.: 13/882,696

(22) PCT Filed: Oct. 31, 2011

(86) PCT No.: PCT/EP2011/069108
§ 371 (c)(1),
(2), (4) Date: Apr. 30, 2013

(87) PCT Pub. No.: WO2012/059459
PCT Pub. Date: May 10, 2012

(65) Prior Publication Data
US 2013/0226086 A1    Aug. 29, 2013

Related U.S. Application Data

(60) Provisional application No. 61/432,700, filed on Jan. 14, 2011.

(30) Foreign Application Priority Data

Nov. 3, 2010 (EP) .................................... 10189801

(51) Int. Cl.
*A61M 5/50* (2006.01)
*A61M 5/24* (2006.01)
(Continued)

(52) U.S. Cl.
CPC ................ *A61M 5/50* (2013.01); *A61M 5/24* (2013.01); *A61M 5/32* (2013.01); *A61M 5/326* (2013.01);
(Continued)

(58) Field of Classification Search
CPC .......... A61M 5/50; A61M 5/326; A61M 5/32; A61M 5/24; A61M 2205/583;
(Continued)

(56) References Cited

U.S. PATENT DOCUMENTS 5,062,828 A * 11/1991 Waltz .................. A61M 5/3129
604/125
6,562,002 B1 * 5/2003 Taylor ................... A61M 5/282
604/82

(Continued)

FOREIGN PATENT DOCUMENTS

| JP | H01-178264 A | 7/1989 |
|---|---|---|
| JP | 2007-512932 A | 5/2007 |

(Continued)

OTHER PUBLICATIONS

English Translation of Notice of the Reason of Rejection issued in Japanese Patent Application No. 2013-537104 dated Aug. 21, 2015.

(Continued)

*Primary Examiner* — Kevin C Sirmons
*Assistant Examiner* — Amber Stiles
(74) *Attorney, Agent, or Firm* — McDonnell Boehnen Hulbert & Berghoff LLP

(57) ABSTRACT

A medicated module attachable to a drug delivery device comprising a connecting body configured for attachment to the drug delivery device. A first needle held within a first needle hub of the connecting body and a second needle fixed within a second needle hub of the connecting body. A recess within the connecting body defining a reservoir. The reser-
(Continued)

voir containing at least one dose of a medicament and configured for fluid communication with the first needle. The connecting body further comprises a lockout feature that prevents the medicated module from being reconnected to the drug delivery device after the medicated module has been connected to the drug delivery device a first time.

11 Claims, 15 Drawing Sheets

(51) Int. Cl.
*A61M 5/32* (2006.01)
*A61M 5/178* (2006.01)
*A61M 5/31* (2006.01)

(52) U.S. Cl.
CPC ... *A61M 5/3294* (2013.01); *A61M 2005/1787* (2013.01); *A61M 2005/3142* (2013.01); *A61M 2205/583* (2013.01)

(58) Field of Classification Search
CPC .. A61M 2005/1787; A61M 2005/3142; A61M 5/3294
See application file for complete search history.

(56) References Cited

U.S. PATENT DOCUMENTS

| | | | |
|---|---|---|---|
| 2008/0177238 | A1 | 7/2008 | Follman et al. |
| 2009/0018506 | A1* | 1/2009 | Daily .................. A61J 1/2096 604/136 |

FOREIGN PATENT DOCUMENTS

| | | |
|---|---|---|
| JP | 2008-212645 A | 9/2008 |
| JP | 2008-535636 A | 9/2008 |
| WO | 2005/053778 A1 | 6/2005 |
| WO | 2007/027203 A2 | 3/2007 |
| WO | 2010/100213 A1 | 9/2010 |

OTHER PUBLICATIONS

Form PCT/IB/326, Notification Concerning Transmittal of International Preliminary Report on Patentability.
Japanese Office Action for JP Application No. 2013-537104, mailed Apr. 26, 2016.

\* cited by examiner

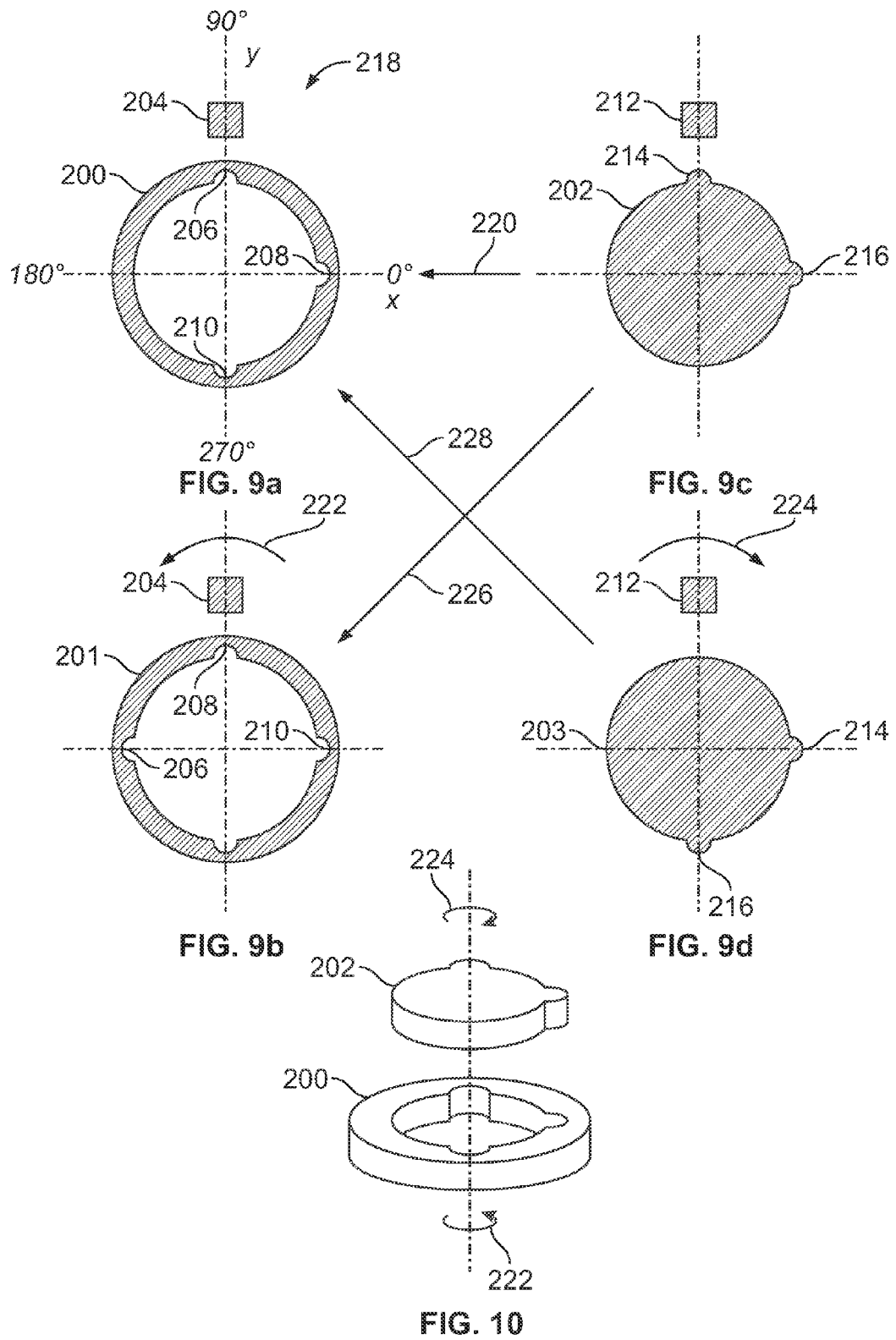

MEDICATED MODULE WITH INTERLOCK

CROSS REFERENCE TO RELATED APPLICATIONS

The present application is a U.S. National Phase Application pursuant to 35 U.S.C. §371 of International Application No. PCT/EP2011/069108 filed Oct. 31, 2011, which claims priority to European Patent Application No. 10189801.3 filed Nov. 3, 2010 and U.S. Patent Application No. 61/432,700 filed Jan. 14, 2011. The entire disclosure contents of these applications are herewith incorporated by reference into the present application.

FIELD OF INVENTION

This invention relates to medical devices and methods of delivering at least two drug agents from separate reservoirs using devices having only a single dose setting mechanism and a single dispense interface. More specifically, the present application is directed to a medicated module comprising an interlock feature that prevents re-connection of the medicated module to a drug delivery device a second time. The medicated module may provide a user an option of priming the device before an injection step. A single delivery procedure initiated by the user causes a non-user settable dose of a second drug agent and a variable set dose of a first drug agent to be delivered to the patient. The drug agents may be available in two or more reservoirs, containers, or packages, each containing independent (single drug compound) or pre-mixed (co-formulated multiple drug compounds). One aspect of our invention is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. This invention is of particular benefit where combination therapy is desirable, but not possible in a single formulation for reasons such as, but not limited to, stability, compromised therapeutic performance and toxicology.

For example, in some cases it might be beneficial to treat a person suffering from diabetes with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, there are certain advantages to storing the active components separately and only combine them at the point of delivery, e.g. injection, need-less injection, pumps, or inhalation. However, the process for combining the two agents needs to be simple and convenient for the user to perform reliably, repeatedly and safely.

A further concern is that the quantities and/or proportions of each active agent making up the combination therapy may need to be varied for each user or at different stages of their therapy. For example, one or more active agents may require a titration period to gradually introduce a patient to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional concerns arise where a multi-drug compound therapy is required, because certain users cannot cope with having to use more than one drug delivery system or make the necessary accurate calculation of the required dose combination. This is especially true for users with dexterity or computational difficulties.

Other problems arise where a user may attempt to re-use a non-sterile needle after a certain dose combination has been delivered. Using such a non-sterile needle could lead to the transmission of certain diseases and therefore there exists a need for a medicated module that prevents needle re-use. There is a further concern of inadvertent needle sticks for care workers/healthcare professionals with certain needle assemblies where the injection needle is not concealed or covered. As such, there is also a general need to reduce certain patient's needle anxiety that may heighten a patient's fear or phobia of exposed needles.

Accordingly, there exists a strong need to provide devices and methods for the delivery of two or more medicaments in a single injection or delivery step that is simple and safe for the user to perform and that also tends to reduce a patient's anxiety towards injections or needles. The present application discloses methods and devices that overcome the above-mentioned concerns by providing separate storage containers for two or more active drug agents that are then only combined and/or delivered to the patient during a single delivery procedure.

Setting a dose of one medicament automatically fixes or determines the dose of the second medicament (i.e., a non-user settable dose). The present application also gives the opportunity for varying the quantity of one or both medicaments. For example, one fluid quantity can be varied by changing the properties of the injection device (e.g., dialing a user variable dose or changing the device's "fixed" dose). The second fluid quantity can be changed by manufacturing a variety of secondary drug containing packages or kits with each variant containing a different volume and/or concentration of the second active agent. The user or healthcare professional would then select the most appropriate secondary package or series or combination of series of different packages or kits for a particular treatment regime.

These and other advantages will become evident from the following more detailed description of the invention.

SUMMARY

The present application discloses modules, systems and methods that allow for the complex combination of multiple drug compounds within a single drug delivery system. Preferably, such a system includes a needle guard that functions to prevent needle reuse and that can also function to reduce needle phobia while also reducing potential inadvertent needle sticks. In addition, such system and devices provide the user an option of priming the device before an injection step. In addition, such system and devices provide an interlock that prevents reconnecting the module to the drug delivery device a second time.

A user can set and dispense a multi-drug compound device through one single dose setting mechanism and a single drug dispense interface. Preferably, the single drug dispense interface may then be locked out so as to prevent reuse of a medicated module (i.e., re-insertion of the injection needle). This single dose setter controls the mechanism of the device such that a predefined combination of the individual drug compounds is delivered when a single dose of one of the medicaments is set and dispensed through the single drug dispense interface.

By defining the therapeutic relationship between the individual drug compounds our delivery device would help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or gases that are capable of flowing and that change shape at a steady rate when acted upon by a force tending to change its shape. Alternatively, one of the medicaments may be a solid that is carried, solubilized or otherwise dispensed with another fluid medicament.

This invention is of particular benefit to patients with dexterity or computational difficulties as the single input and associated predefined therapeutic profile removes the need for them to calculate their prescribed dose every time they use the device and the single input allows considerably easier setting and dispensing of the combined compounds. This invention is also of particular benefit to patients experiencing needle phobia or who may experience a general fear of inadvertent needle sticks.

In a preferred embodiment a master drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro (B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys- Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one arrangement, a medicated module attachable to a drug delivery device comprises a connecting body configured for attachment to the drug delivery device. A first needle is fixed within a first needle hub of the connecting body and a second needle is fixed within a second needle hub of the connecting body. A recess within the connecting body defines a reservoir containing at least one dose of a medicament. The reservoir is configured for fluid communication with the first needle. The connecting body further comprises a lockout feature that prevents the medicated module from being reconnected to the same drug delivery device after the medicated module has been connected to the drug delivery device a first time and then subsequently removed (with or without dispensing a dose).

In an alternative arrangement, a medicated module attachable to a drug delivery device comprises a connecting body configured for attachment to the drug delivery device. A first needle is held within a first needle hub of the connecting body and a second needle is held within a second needle hub of the connecting body. A bellows (herein, also referred to as a membrane) containing a priming fluid is configured for fluid communication with the second needle.

In another example, Applicants' concept provides a connection means for a medicated module that is capable of accommodating safe dose splitting between two drug delivery devices (e.g., split dosing necessitated by the end of a cartridge) through the use of mechanical means. The mechanical means allows a new medicated module to be fitted to either a new (i.e., unused) drug delivery device or one that has been previously used. The mechanical means of Applicants' proposed concept also allows a previously-used medicated module to be fitted to a new (i.e., unused) device but not to a previously-used drug delivery device. Further, after two uses, the medicated module may be locked out and prevented from further use. Thus, a medicated module in accordance with Applicants' proposed concept may be used with (i) a single drug delivery device for two injections (where the second injection would be of a single medicament in an situation where the user needed to split their dose for volume or injection site reasons) or (ii) a first drug delivery device and a second new drug delivery device for two injections (where the user needs to split their dose of the user variable medicament because there is not enough left within one device to deliver all of the required dose).

A particular benefit of our invention is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc., so that a patient could be instructed to use the supplied medicated module in a specific order to facilitate titration. Alternatively, the prescribing physician may provide the patient with a number of "level one" titration medicated modules or a kit of modules and then when these were finished, the physician could then prescribe the next level or the next drug delivery kit. A key advantage of this titration program is that the primary device can remain constant throughout.

In a preferred embodiment, the primary drug delivery device is used more than once and therefore is multi-use. Such a device may or may not have a replaceable reservoir of the primary drug compound, but our invention is equally applicable to both scenarios. It is possible to have a suite of different medicated modules for various conditions that could be prescribed as one-off extra medication to patients already using a standard drug delivery device. Should the patient attempt to reuse a previously used medicated module, the presently disclosed medicament module also may provide a lockable needle guard feature that could alert the patient to this situation. Other means of alerting the user may include some (or all) of the following:

Physical prevention of medicated module re-attachment to the primary drug deliver device once the module has been used and removed.

Physical prevention of insertion of the used drug dispense interface into the patient (e.g., a single use needle-guard type arrangement).

Physical/hydraulic prevention of subsequent liquid flow through the drug dispense interface once it has been used.

Physical locking of the dose setter and/or dose button of the primary drug delivery device.

Visual warnings (e.g., change in color and/or warning text/indicia within an indication window on the module once insertion and/or fluid flow has occurred).

Tactile feedback (presence or absence of tactile features on the outer surface of the module hub following use).

A further feature of this embodiment is that it provides a user with an optional priming step while also, in a subsequent step, provides for both medicaments to be delivered via one injection needle and in one injection step. This offers a convenient benefit to the user in terms of reduced user steps compared to administering two separate injections. This benefit may also result in improved compliance with the prescribed therapy, particularly for users who find a priming step challenging or difficult or where a patient's fear of injections as being unpleasant or painful or for patients who have computational or dexterity difficulties.

The present application is also directed to a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

A further independent aspect of the invention relates to a drug delivery system comprising a drug delivery device. The drug delivery device comprises a dose setting mechanism, a reservoir holder coupled to the dose setting mechanism, wherein a distal end of the reservoir holder is configured for attaching a medicated module according to the invention described herein. Further, the system comprises such a medicated module. The system comprises a mechanical logic feature configured for (i) allowing a first use of the medicated module, (ii) allowing a subsequent use of the medicated module, wherein the second use occurs prior to the medicated module being detached from the drug delivery device and (iii) preventing subsequent uses of the medicated module once removed.

In a further embodiment, the mechanical logic feature may be further configured to, after allowing the use of the first medicated module, prevent a subsequent use of a second medicated module different than the first medicated module.

In another embodiment, the mechanical logic feature comprises (i) a fixed alignment feature and (ii) a plurality of coded features; wherein the corresponding mechanical logic feature of the medicated module comprises (i) a corresponding fixed alignment feature and (ii) at least one corresponding coded feature that corresponds to the each of the plurality of coded features of the mechanical logic feature of the drug delivery device. The at least one corresponding coded feature may be disposed on an outer wall of a core mechanism of the medicated module. The interaction of the plurality of coded features of the mechanical logic feature of the drug delivery device and the corresponding coding features serves to change a state of the drug delivery device from unused to used.

In a further embodiment the drug delivery system according to the invention disclosed herein comprises a mechanical logic feature, wherein at least part of the mechanical logic feature is part of the drug delivery device according the invention in this disclosure.

A further independent aspect of the invention relates to a drug delivery device according to the invention of the present disclosure These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIG. 9a depicts a cross-sectional view of an exemplary unused (i.e., new) medical delivery device;

FIG. 9b depicts a cross-sectional view of an exemplary used (i.e., triggered) medical delivery device;

FIG. 9c depicts a cross-sectional view of an exemplary unused (i.e., new) medicated module;

FIG. 9d depicts a cross-sectional view of an exemplary used medicated module;

FIG. 10 depicts a perspective view of a cross-section of an exemplary drug delivery and a cross-section of an exemplary medicated module;

FIG. 12b depicts a cross-sectional view of the exemplary medical delivery device of FIG. 12a being attached to the exemplary medicated module of FIG. 12a;

FIG. 14a depicts a key 400 that illustrates an example split dosing scheme;

FIG. 14b is a flow chart that illustrates the example split dosing scheme shown in FIG. 14a;

FIG. 15 is a more detailed flow chart that illustrates the example split dosing scheme of FIG. 14a;

DETAILED DESCRIPTION

The present application is directed to a system and method for administering a fixed predetermined dose of a second medicament (secondary drug compound) and a potentially variable dose of a first medicament (primary drug compound) through a single output or drug dispense interface. Setting the dose of the primary medicament by the user automatically determines the fixed dose of the second medicament. This fixed dose of the second medicament is preferably a single dose. In a preferred arrangement, the drug dispense interface comprises a needle cannula (hollow needle). The system may include a needle guard that may be locked out after the medicated module has been disconnected from a drug delivery device or removed from the injection site. The present application also allows a user to prime an injection needle with a priming fluid contained within a drug delivery device.

Figure 1:
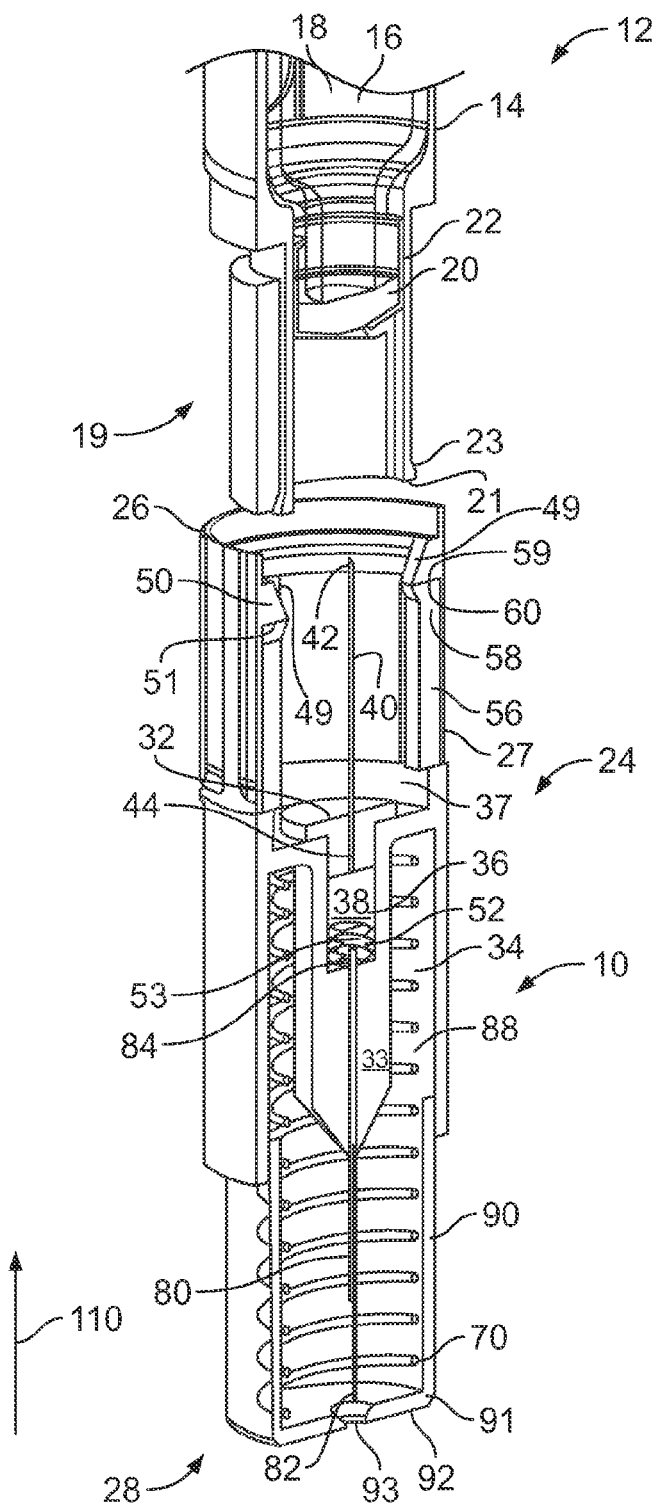
FIG. 1 illustrates one arrangement of a medicated module that can be attached to a drug delivery device.

FIG. 1 illustrates a preferred arrangement of a medicated module 10. FIG. 1 also illustrates a distal end of a drug delivery device that is configured for connection to the medicated module 10.

The medicated module 10 comprises a connecting body 24, a first or proximal needle 40, a locking ring 56, a bellows arrangement 52, a second or distal needle 80, a biasing element 70, and a needle guard 90.

The connecting body 24 has a generally cylindrical shape and extends from a proximal end 26 to a distal end 28. At the proximal end of the connecting body, the medicated module is provided with ratchet tabs 50. These ratchet tabs 50 are configured with inwardly and downwardly directed surfaces 49 below which the tabs comprise a bottom flat surface 51. This configuration acts as a lockout feature to prevent a user from reconnecting these ratchet tabs with the pawls provided on the cartridge housing a second time.

Internally, the connecting body 24 defines a first or distal inner portion 34 and a second or proximal inner portion 37. At a distal most portion of the first portion 34, the medicated module 10 further comprises a bellows arrangement 52 positioned in the first inner portion 34 between a reservoir 36 and a proximal end of the second needle 80. This bellows arrangement comprises a deformable reservoir made from a pierceable material. It might be beneficial for the membrane/bellows to be produced from a material that is broadly inert when placed into long term contact with either the first or second medicament and that offers good performance with respect to leachables and/or extractables. Potential materials that this application could include, but are not limited to; TPE (Thermoplastic Elastomers), Liquid Silicone Rubber (LSR) and natural rubbers. Alternative materials, including Low-density Polyethylene (LDPE) or Linear low-density Polyethylene (LLDPE) are also possible. Where improved barrier properties are desirable, laminate materials may be used e.g. multilayer materials consisting of the primary membrane material (potentially as above) plus additional thin layers of materials like PVC (Polyvinyl chloride) PCTFE (Polychlorotrifluoro ethylene) or Aluminum. The nature of the use of material would require it to be collapsible in some way. This is fine for the flexible materials mentioned; however for the more rigid ones the bellows design may incorporate a series of live hinges to permit collapsing of a semi-rigid component. Preferably, the bellows arrangement 52 defines an inner volume that contains a reservoir of a priming fluid 38. Most preferably, this priming fluid comprises a priming amount of a medicament similar to the primary medicament contained within the drug delivery device.

In addition, the first portion 34 is formed so as to define a cavity or reservoir 36 containing a secondary medicament 38 and is directly adjacent this bellows arrangement 52. Preferably, this reservoir 36 contains a single dose of the secondary medicament. More preferably, the reservoir contains a dose of an active agent such as a GLP-1.

The first inner portion 34 is configured to retain a biasing element 70. The distal end of the connecting body is provided with a needle guard 90 which is biased by this biasing element 70. As illustrated in FIG. 1, the biasing element 70 is in an extended state and extends the needle guard to cover the second needle 80. The needle guard 90 is slidably coupled to an inner wall surface 88 of the distal end of the connecting body 24.

Prior to being connected to the drug delivery device 12, the needle guard is locked in this extended position and is prevented from moving in the proximal direction. Preferably, both the connecting body 24, the locking ring 56, and the cartridge holder comprise aligning slots so as to require alignment of all three slots before the needle guard 90 is allowed to move.

The alignment of all three of these slots is described in greater detail with reference to FIGS. 6a, 6b, and 6c. In some examples, in order to be able to attach to the medicated module 10, the cartridge holder 14 has to be rotationally aligned with the locking ring 56. This alignment provides the ability to turn the internal locking ring 56 to line up slots created by the aligned locking ring and cartridge holder 14 with the needle guard 90.

Figure 6A:
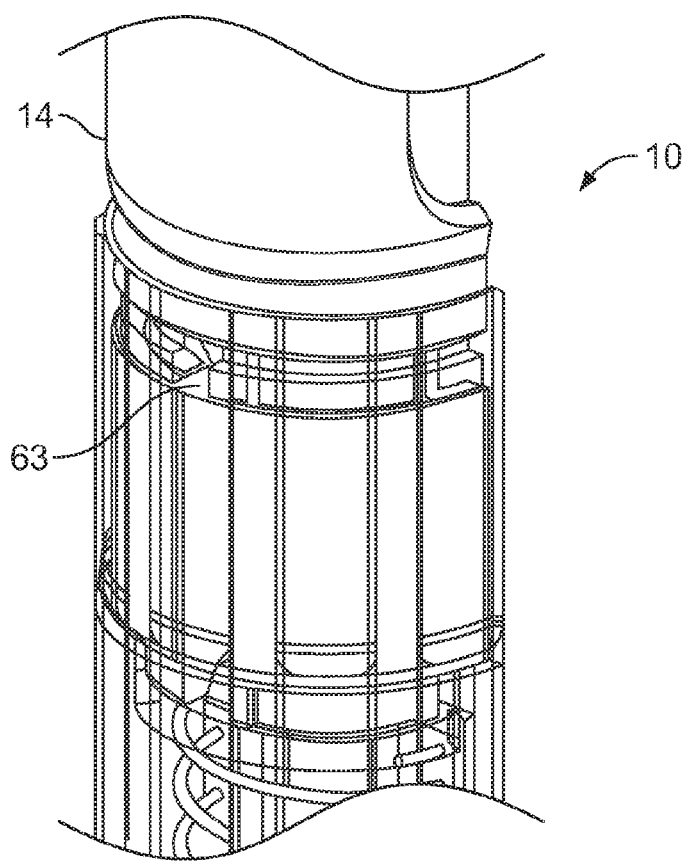
FIG. 6a illustrates a perspective sectional view of the medical module attached to the drug delivery device illustrated in FIG. 1.
Figure 6B:
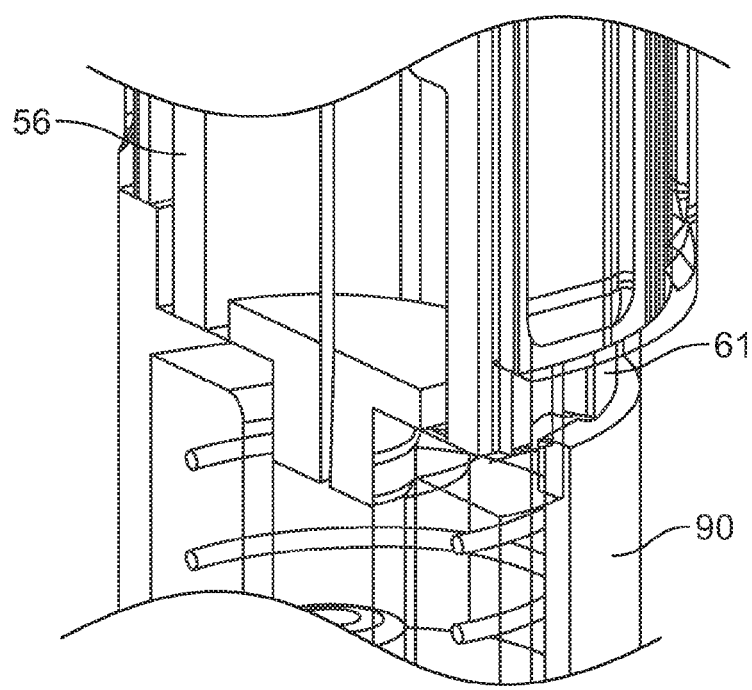
FIG. 6b illustrates another perspective sectional view of the medical module attached to the drug delivery device illustrated in FIG. 1, where the needle guard is prevented from moving axially.
Figure 6C:
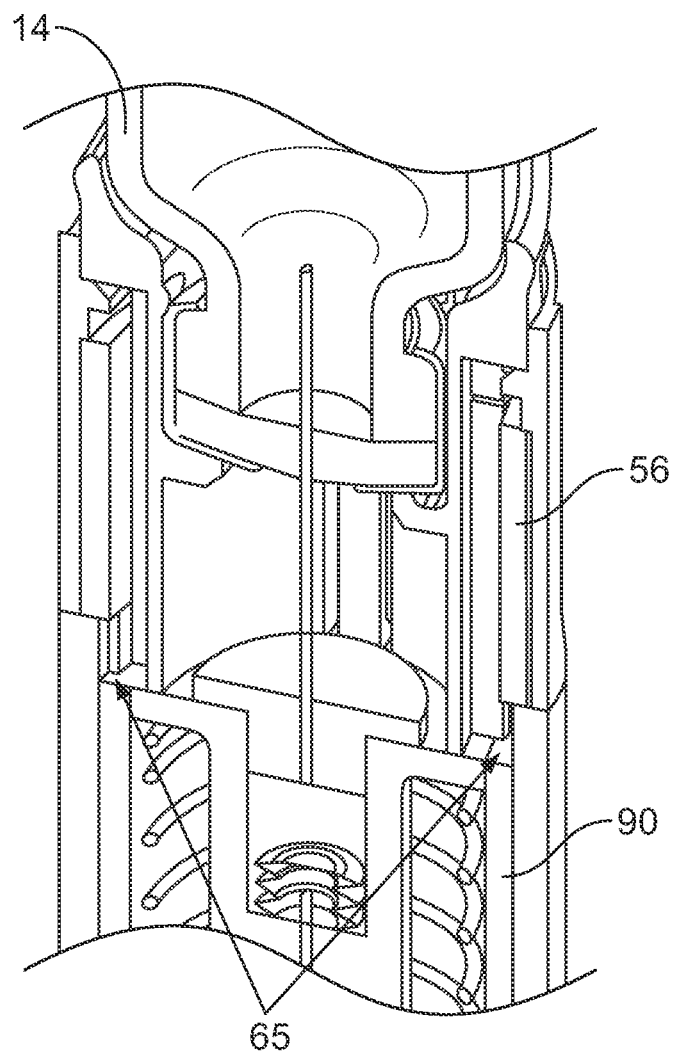
FIG. 6c illustrates another perspective sectional view of the medical module attached to the drug delivery device illustrated in FIG. 1.

As shown in FIG. 6a-b, the cartridge holder and the locking ring may comprise ribs and splines, such as rib 61 on the cartridge holder 14 and spline 63 on the locking ring 56. When the ribs/splines of the cartridge holder and locking ring are aligned, the locking ring can be turned to line up slots in the locking ring/cartridge holder with the needle guard 90. As shown in FIG. 6b, prior to turning the cartridge holder 14, the needle guard 90 is prevented from moving axially because of the ribs 61 on the cartridge holder 14. However, as shown in FIG. 6c, once the locking ring 56 and the cartridge holder 14 have been turned, slots 65 line up properly with the needle guard 90 so that the needle guard 90 may axially retract. Note that continuing this turning to remove the device will result in the needle guard being locked again in a similar manner.

Returning to FIG. 1, while the needle guard 90 resides in the extended position, it substantially conceals the second needle 80 from a user's view so as to help reduce any needle anxiety that a patient may be experiencing. While substantially concealing the second needle, the needle guard 90 also helps to prevent inadvertent needle sticks. As described in greater detail below, prior to an injection, a user orientates the various slots on the connecting body 24, locking ring 56, and cartridge holder 14 so as to allow proximal movement of the needle guard. Then, during an injection step, the needle guard 90 is free to move in a proximal direction or towards the drug delivery device (illustrated by arrow 110 in FIG. 1). Furthermore, the needle guard 90 may comprise a rotation preventor so as to prevent the needle guard 90 from rotating, either when connected to the drug delivery device or during a priming or an injection step, until such time as decided by the user.

The connecting body further comprises a first or proximal needle hub 32 and a second or distal needle hub 33. The first needle hub is positioned so as to provide a fluid seal over the proximal end of the reservoir 36. A first needle 40 is rigidly held in the first needle hub 32. Preferably, this first needle 40 comprises a first piercing end 42 (i.e., a proximal end) for piercing the membrane 20 of the cartridge assembly 16 contained within the drug delivery device 12. In addition, the first needle 40 comprises a second end 44 (i.e., a distal end) that is in fluid communication with the reservoir 36 and hence the secondary medicament 38 contained therein.

The second needle 80 is fixedly held in the second needle hub 33. This second needle 80 comprises a piercing distal end 82 so as to axially move through a pass through 93 in the needle guard 90 to penetrate an injection site, such as a human injection site. As can be seen from FIG. 1, a proximal end 84 of the second needle 80 is in fluid communication with the priming fluid 53 contained within the bellows 52.

The second or proximal portion 37 of the connecting body 24 further comprises a locking ring 56. In FIG. 1, this locking ring 56 is illustrated as being seated within a groove 27 along an inner wall near the proximal end 26 of the connecting body 24. As illustrated, the locking ring 56 resides in a first position or a pre-connection position. This locking ring 56 includes ratchet tabs 58 located near the proximal end of the medicated module 10. At a proximal end of the locking ring, these ratchet tabs 58 have a generally flat top surface 60. As will be discussed in greater detail below, these ratchet tabs 58 cooperate with a pawl arrangement provided near a distal end of a cartridge housing of the drug delivery device 12 so that the medicated module 10 may be connected to and disconnected from a distal end of the drug delivery device 12. In one particularly preferred arrangement, this ratchet tab and pawl arrangement act as a lockout feature to prevent an expended medicated module from being reattached to a drug delivery device. These ratchet tabs 58 may prevent re-attachment. These ratchet tabs have an upper flat section and a lower angled section. When in line with the other tabs as described here, a cartridge holder can be attached as the top tab causes deflection of the pawl on the way in. After turning the cartridge holder, these sets of tabs may not be axially aligned. The cartridge holder can be pulled out due to the sloping lower face on the locking ring. However, if attempt is made to reattach, although the upper tabs can deflect the pawls, the flat upper surface on the locking ring tabs prevents the cartridge holder from travelling further axially and consequently not attaching.

The medicated module 10 is preferably self-contained and may be provided as a sealed and sterile disposable module. Although not shown, the medicated module 10 could be supplied by a manufacturer contained in a protective and sterile capsule or container where the user would peel or rip open a seal or the container itself to gain access to the sterile medicated module. In some instances it might be desirable to provide two or more seals for each end of the medicated module.

Figure 8:
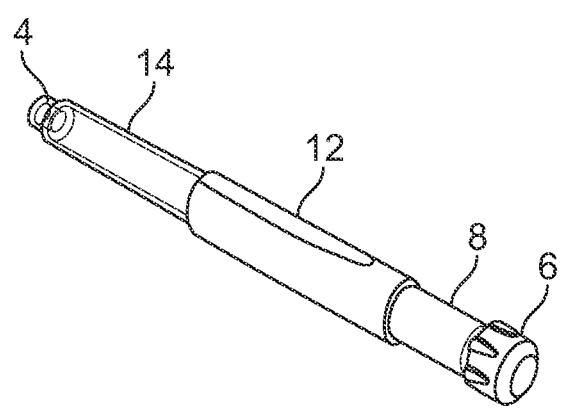
FIG. 8 illustrates one possible drug delivery device that can be used with the medicated module illustrated in FIG. 1

In this preferred arrangement, the medicated module 10 may be removably attached to a cartridge housing 14 of a drug delivery device 12, such as a pen type drug delivery device. Only a portion of such a drug delivery device 12 is illustrated in FIG. 1. Such drug delivery device 12 could comprise a pen type drug delivery device 12 as illustrated in FIG. 8. This drug delivery device 12 comprises a cartridge housing 14 coupled to the dose setting mechanism 1 The cartridge housing 14 contains either a removable or non-removable cartridge assembly containing a primary medicament, such as an insulin. To set a dose of the primary medicament, a double ended needle assembly is connected to the distal end 4 of the cartridge holder 14. Then, the dose setter 8 is rotated to a desired dose. To inject this set dose, the dose button 6 is pushed forward.

Returning to FIG. 1, the drug delivery device 12 comprises a ratchet pawl arrangement 19 at its distal end. In one arrangement, this ratchet pawl arrangement can be form fitted or snap locked onto a distal end of a cartridge holder, such as the cartridge holder 14 of the device 12 illustrated in FIG. 8. Alternatively, the ratchet pawl arrangement 19 may be manufactured as an integral component of the cartridge holder 14.

The cartridge holder 14 contains a medicament reservoir, such as a standard cartridge assembly 16. Where the drug delivery device 12 comprises a drug delivery device that can be reset (e.g., a pen type device where the piston rod can be reset), the cartridge assembly 16 can be removed from the cartridge housing 14 and replaced with a fresh cartridge assembly. Alternatively, the drug delivery device for use with Applicants' medicated module may comprise a disposable device. With such a disposable device, the cartridge assembly 16 is not user removable and therefore the entire drug delivery device is discarded once the primary medicament in the device has been expended either in one single dose or multiple fixed or variable doses.

Preferably, cartridge assembly 16 comprises a reservoir for holding a primary medicament 18. Such primary medicament may be an insulin, such as a long acting or a short acting insulin. The cartridge assembly 16 further comprises a pierceable membrane 20 held in place in part by way of a ferrule 22. Ferrule 22 could comprise a metallic ferule or a molded ferule.

Figure 2:
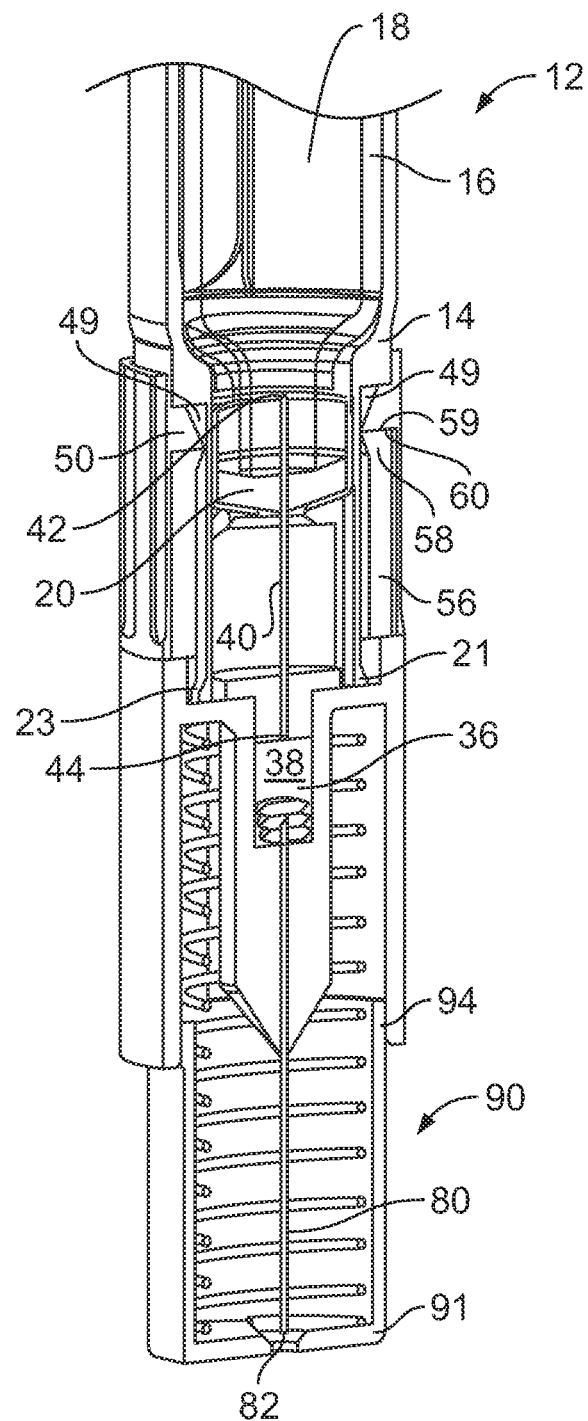
FIG. 2 illustrates a cross-sectional view of the medical module attached to the drug delivery device illustrated in FIG. 1.

FIG. 2 illustrates a perspective side view of the medicated module 10 initially connected to the drug delivery device 12. In order to connect the medicated module 10 to the drug delivery device 12, the distal end of the cartridge holder 14 is inserted into the proximal end 26 of the connecting body 24. During insertion, the outwardly angled faces 23 of the ratchet tabs 21 initially slide along and then over the inwardly and downwardly angled faces 49 of the ratchet tabs 50 in the connecting body 24. This causes the ratchet pawls of the cartridge holder 14 to initially deflect towards an inner space of the connecting body 24. Because of their elastic nature, these ratchet pawls 21 spring back to their previous steady state position as illustrated in FIG. 2.

The connecting body ratchet tabs 50 will then align themselves with the ratchet tabs 58 provided on the locking ring 56. This interconnection may be seen from FIG. 2 which illustrates the medicated module 10 initially correctly aligned with the distal end of the drug delivery device 12.

When the medicated module 10 is initially connected to the drug delivery device 12, the proximal piercing end 42 of the first needle 40 pierces the membrane 20 of the cartridge assembly 16. Since the second end 44 of this first needle 40 will then be in fluid communication with the medicament 18 contained within the reservoir 46, the primary medicament 18 contained in the cartridge assembly 16 will be in fluid communication with the secondary medicament 38 contained in the reservoir 46.

Figure 3:
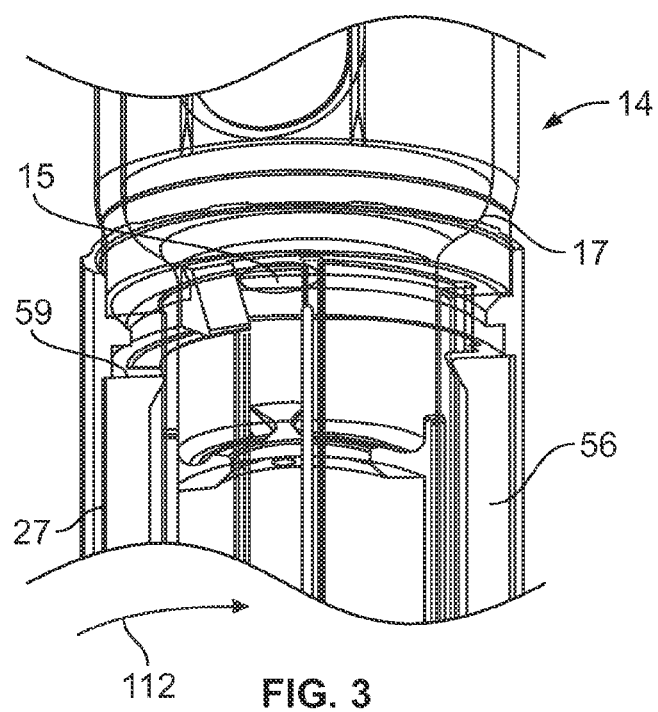
FIG. 3 illustrates a side perspective view of the medical module attached to the drug delivery device illustrated in FIG. 1 after the medicated module has been rotated.

FIG. 3 illustrates a subsequent step of mounting the medicated module 10 onto the cartridge holder of the drug delivery device 12 after initial alignment of the medicated module and drug delivery device as illustrated in FIG. 2. As illustrated in FIG. 3, after the cartridge holder 14 is initially inserted into connecting body 24, the user or other healthcare provider is called upon to rotate the medicated module 10. Preferably the medicated module must be rotated in a counter clock wise direction and this counter clock wise direction is illustrated by arrow 112.

As the medicated module 10 is rotated in direction 112, movement of the medicated module causes the connecting body ratchet tabs 50 to rotate around a groove 15 situated along a recessed surface 17 of the cartridge holder 14. As such, the flat bottom portion 51 of the connecting body ratchet tab 50 will no longer be in alignment with the upper flat surface 59 of the locking ring 56 as it runs within this groove 15. It is this misalignment that retains the cartridge holder to the medicated module through the interaction of connecting body ratchet tab and the cartridge holder groove.

After this rotational step, the locking ring 56 remains in a vertical groove of the connecting body which is a bayonet groove located above the top surface of the locking ring 56. Therefore, during this rotational step indicated by arrow 112 in FIG. 3, the locking ring 56 remains stationary relative to the cartridge holder 14.

Figure 4:
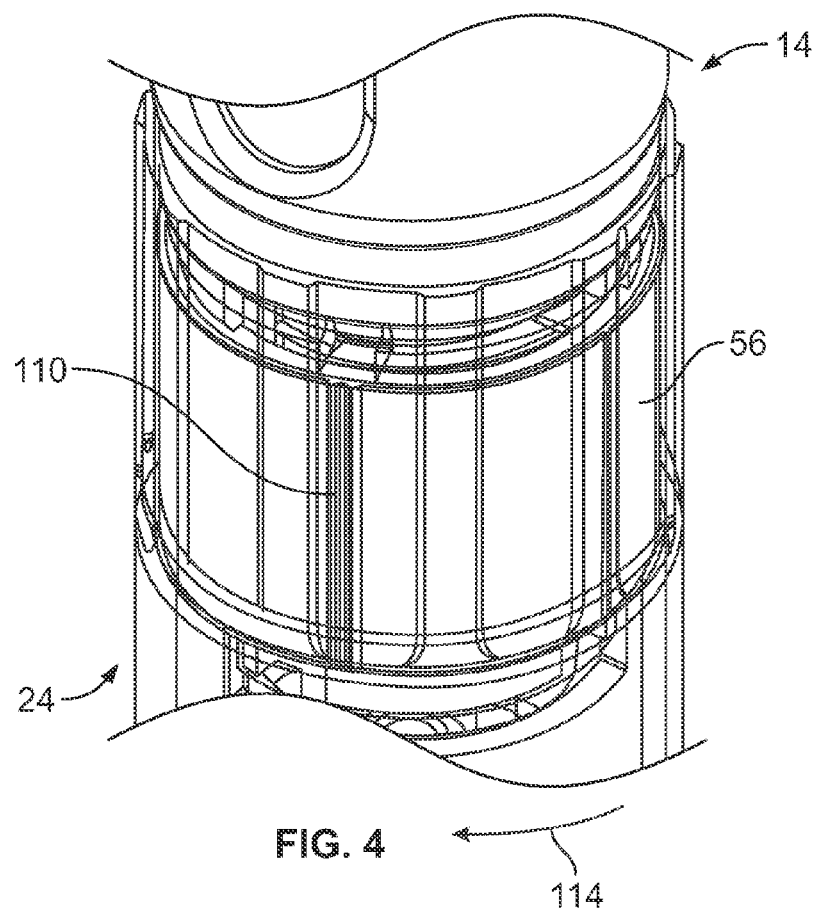
FIG. 4 illustrates a partial perspective view of the medicated module connected to the drug delivery device.

As may be seen from FIG. 4 and FIGS. 6a-6c, slots are provided along an inner surface of the medicated module 10, along an inner surface of the locking ring, and also along an inner surface of the cartridge holder. After completing the rotational step discussed above, these three slots will be in alignment and this alignment is illustrated in FIG. 4. When these slots are in alignment, the needle guard 90 of the medicated module 10 is allowed to move in the proximal direction against the force exerted by the biasing member 70.

Preferably, an indent feature 110 is provided between the locking ring 56 and connecting body 24 of the medicated module 10. In this manner, during rotation in direction 114 the indent feature 110 indicates to a user that the medicated module 10 has been sufficiently rotated so as to allow the needle guard 90 to move in an upwards direction and retain the cartridge holder and module together for use. In one preferred arrangement, the indent feature may comprise ramp shaped features such that once these features are engaged, the medicated module can no longer be rotated in a counter clockwise direction so as to return the medicated module back to the initial unused position as illustrated in FIG. 2.

Figure 5:
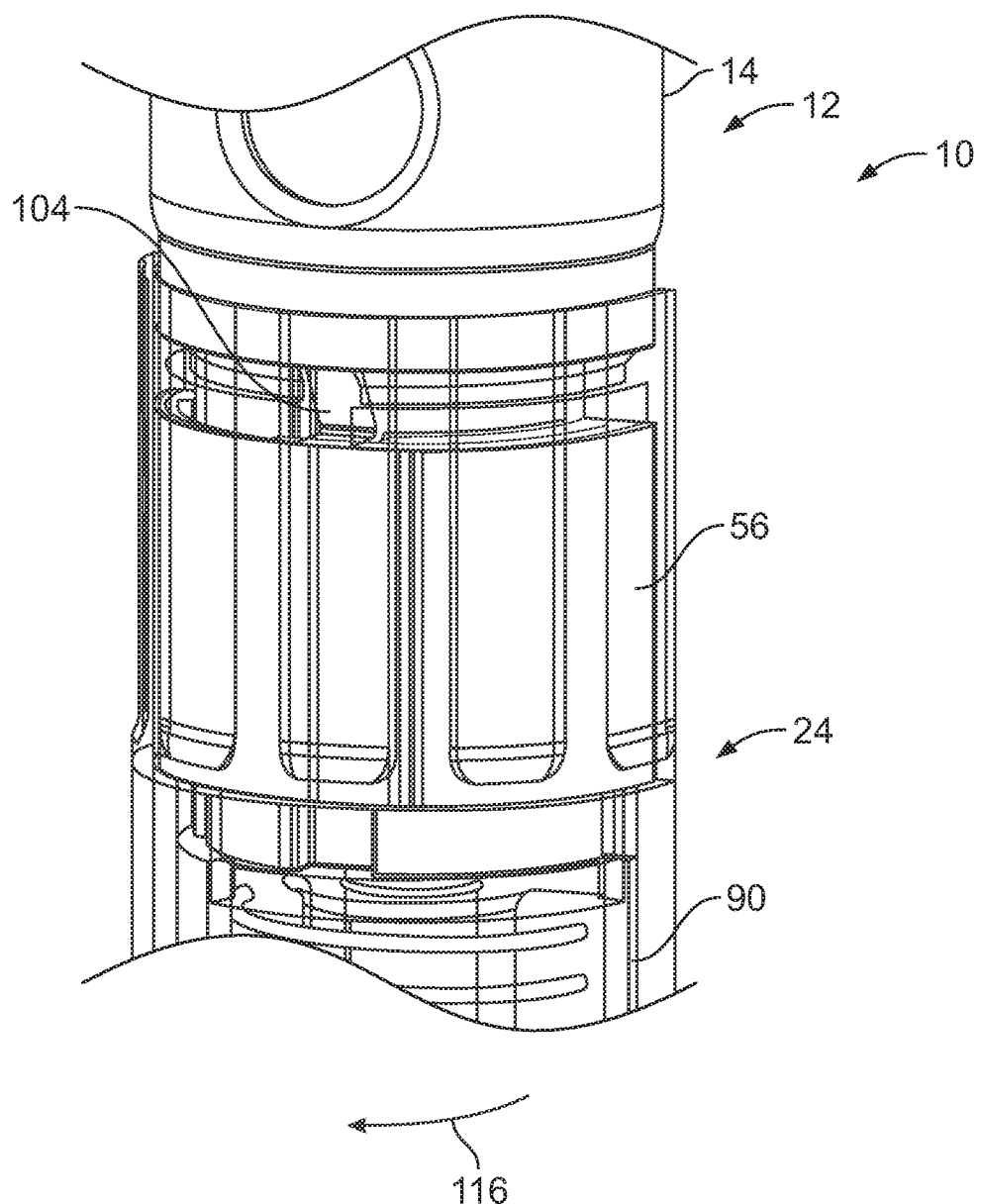
FIG. 5 illustrates a partial perspective view of the medicated module connected to the drug delivery device.

The medicated module 10 illustrated in FIG. 5 now resides in a priming state. In this priming state, the medicated module 10 allows a user to prime the medicated module with the priming fluid 53 contained within the bellows arrangement 52. This priming step occurs before the dialing and dispensing and injection of both the primary medicament 18 from the cartridge assembly 16 and secondary medicament 38 contained within the reservoir 36.

As explained below, in this priming position, the first needle 40 is in fluid engagement with the reservoir 36 and the second needle 80 is in fluid communication with the priming fluid 53 contained in the bellows 52.

During priming, the primary medicament from the primary device is dispensed into the cavity containing the second medicament. This causes the bellows to compress and therefore displaces the priming fluid from the bellows through the second needle 80. At the end of this priming step, the bellows compresses such that the piercing proximal end 84 of the second needle 80 pierces a top surface of the bellows 52. This then allows fluid communication between the secondary medicament 38 and the second needle 80 for the proper injected dose.

Figure 17:
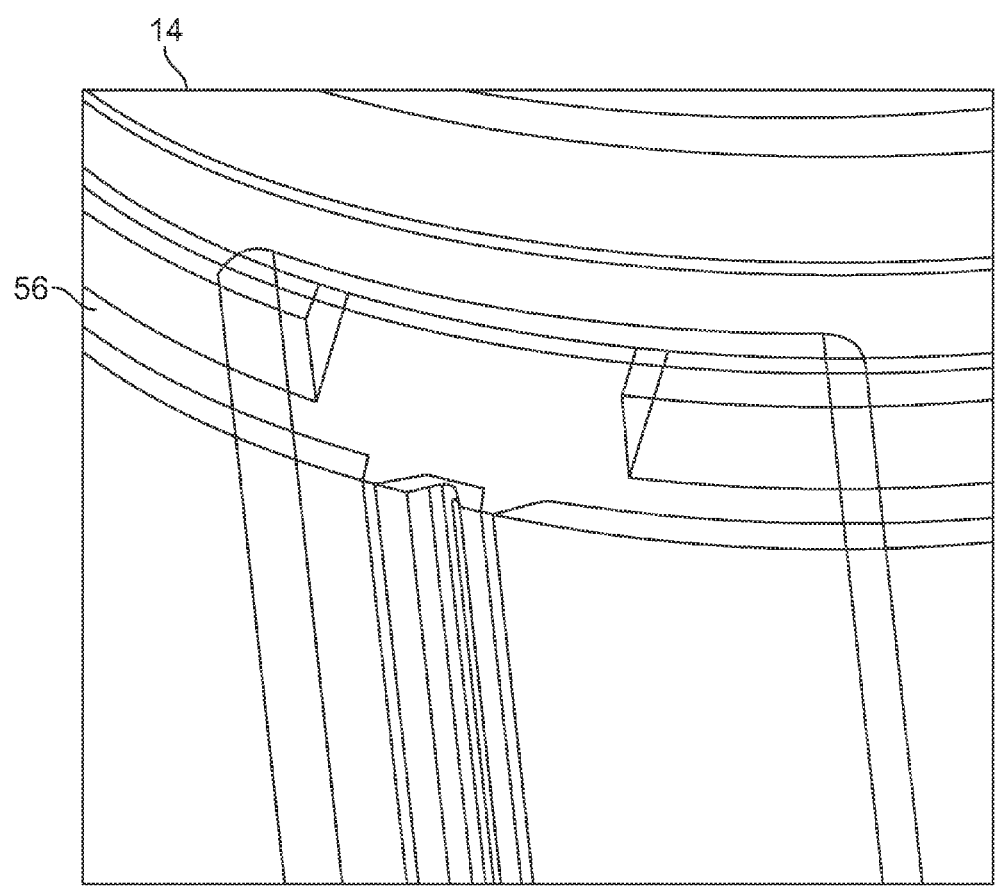
FIG. 17 illustrates the medicated module and drug delivery device illustrated in FIG. 1 in a post-turning detent position.

In an example, the locking collar and cartridge holder may enter a post-turning detent position. This post-turning detent position is illustrated in FIG. 17. The drug delivery device may be primed after entering this detent position. However, in other examples, the device could be primed without turning to this position. When the device is in this post-turning detent position, the needle guard is unlocked and therefore capable of injection. If primed before entering this detent position, there would be less of a chance of a user injecting the priming dose as the needle guard would still be locked down.

Where the drug delivery device 12 comprises a dose setter 8, a dose of the drug delivery device 12 may then be set using a dose setter 8 (see FIG. 8) in the normal manner (e.g., by dialing out the appropriate number of units). Dispense of the medicament 38 may then be achieved by subcutaneously injecting the medicaments via activation of a dose button on device 12. The dose button 6 may be any triggering mechanism that causes the dose of the first medicament that was set by the dose setter to move distally towards the distal end of the device. In a preferred embodiment, the dose button is operably connected to a spindle that engages a piston in the primary reservoir of the first medicament.

After injection, the drug delivery device and the medicated module are removed from the injection site, the needle guard 90 under the force of the biasing element 70 is forced in the distal direction 110. After use and when the needle guard is in the down position, the medicated module can be rotated further as illustrated in FIG. 5 in direction 116. The medicated module 10 can be rotated past another indent feature until the module 10 reaches an end stop 104 on the bayonet groove 102 of the cartridge holder 14. It is only in this position that the medicated module 10 can now be removed from the cartridge holder.

Figure 7:
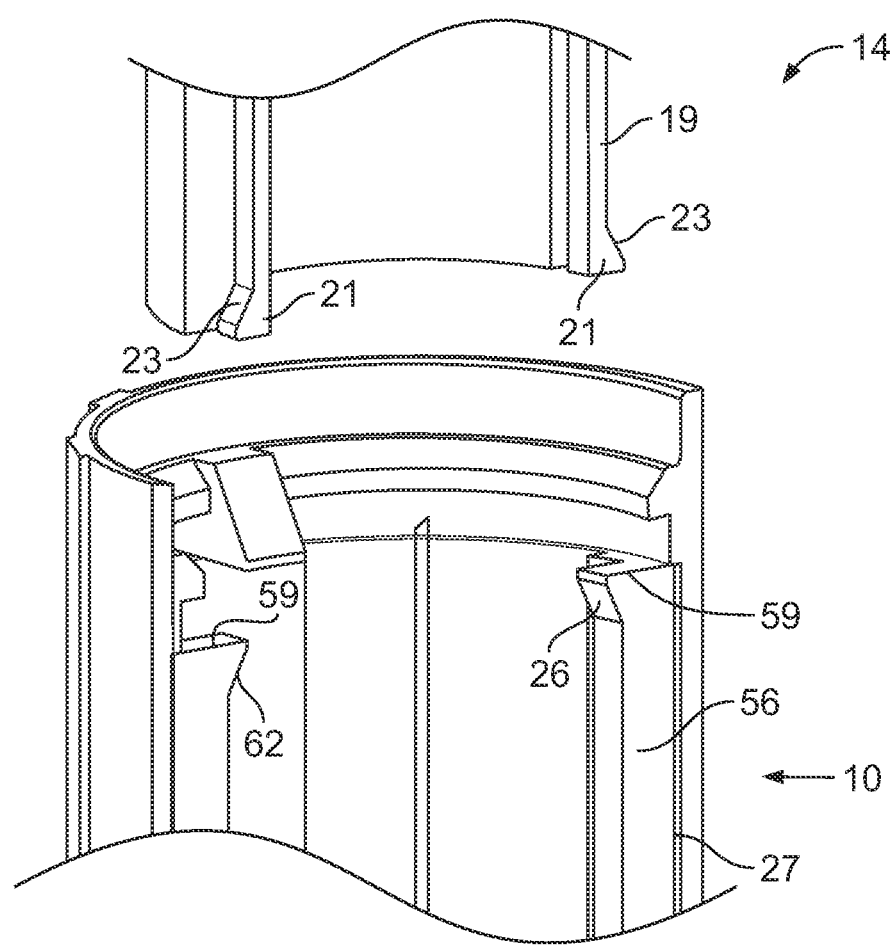
FIG. 7 illustrates the medicated module of FIG. 6 removed from the drug delivery device.

FIG. 7 illustrates an expended medicated module 10 from the pawl arrangement 19 of the cartridge holder 14. Upon removal of the medicated module 10, the angled face 23 on the ratchet pawl 21 contacts the inwardly and upwardly directed angled faces 62 along the locking ring 56. This interaction causes the pawl to deflect inwardly to therefore allow removal of the module from the cartridge housing 14. Therefore, as illustrated, if a user were to attempt to re-attach the expended medicated module 10, the flat top surface 59 of the ratchet tabs 58 on the locking ring 56 would prevent the pawls 21 from reattaching to the module 10.

Use of Applicants' interlocking feature with such a medicated module provides a number of advantages. First, such an interlocking feature prevents a user from re-using a non-sterile medicated module (through re-attachment to a device after having previously removed). Second, with Applicant's proposed pawl design, only certain cartridge housings having a cooperating pawl receiving means can cooperatively work with such a medicated module. This restricts the types of medicaments that may be used with the medicated module and therefore prevents a user from injecting a non-preferred drug with the drug contained within the cavity of the medicated module. In addition, with Applicants' proposed medicated module, the locked needle guard protects and substantially conceals the second needle 80. Therefore, the locked needle guard reduces the risk of a potential inadvertent needle stick, especially for health care workers/healthcare professionals. Moreover, because the locked needle guard substantially conceals the second needle 80, the guard acts to reduce any potential needle fear, needle phobia or needle anxiety that a patient may experience.

As is known in the art, users of drug delivery devices sometimes split their required dose into two (or more) smaller doses. Splitting doses can be done for various reasons. For example, the required or desired dose may be too large. The dose may be too large for the device to deliver in a single action (e.g., a given device may have a maximum dialable volume of 0.8 ml). The dose may also be too large for the injection site to comfortably accommodate the dose (e.g., in some situations, healthcare professionals recommend that their patients split doses over a certain size, some as low as 0.4 ml, into two different sites to prevent pooling or inefficient absorption).

As another exemplary reason for splitting doses, a user nearing the end of a cartridge of medicament may determine that the device has insufficient residual volume left for the user's complete dose (e.g., the user requires a dose volume of 0.4 ml, but the drug delivery device only has 0.3 ml remaining in it). The user may elect to (i) take the remaining medicament from the "old" device nearing the end of a cartridge of medicament, and then (ii) take a replacement device (e.g., a new device) to deliver the remaining fraction of their dose.

As yet another example reason for splitting doses, a user may experience discomfort part way through an injection (e.g., possibly due to injecting into scar tissue from previous injections), and the user may elect to stop the injection stroke, withdraw the needle, and find a second site to deliver the remaining dose into.

In the context of drug delivery devices and systems, split-dosing behavior may need to be balanced with both sterility issues and mono product use issues. Regarding sterility, while it is generally recognized that a reasonable percentage of patients re-use needles (sometimes multiple times), each injection should be ideally done with a sterile needle cannula in order to reduce the risk of increased pain, inflammation, and/or septicemia. When a needle cannula is reused, such reuse is preferably limited to immediately after the first use.

Regarding mono product use, for drugs that are intended to be used in combination, mono product use (e.g., accidentally or consciously just taking one of the constituent compounds) should be avoided. Mono product use may compromise the therapeutic effectiveness of the treatment and increase the risk of short-term risks (e.g., hyperglycemia) or longer-term risks associated with poor disease management.

Applicants' proposed concepts allow for controlled split dosing. Controlling split dosing allows for safe split dosing that balances the need for split dosing with safety issues, such as mono product use and sterility. Applicants' various proposed concepts for controlled split dosing allow a step of split dosing with a given medicated module but preventing further reuse of a medicated module without conscious decision/reason. Additionally, in an embodiment, a used medicated module cannot be used for split dosing with a previously-used device. The controlled split dosing in accordance with one of Applicants' proposed concepts is discussed in more detail below.

In an example, Applicants' concept provides a connection means for a medicated module that is capable of accommodating safe dose splitting between two drug delivery devices (e.g., split dosing necessitated by the end of a cartridge) through the use of mechanical means. The mechanical means allows a new medicated module to be fitted to either a new (i.e., unused) drug delivery device or a drug delivery device that has been previously used. The mechanical means of Applicants' proposed concept also allows a previously-used medicated module to be fitted to a new (i.e., unused) device but not to a previously-used drug delivery device. Further, after a plurality of uses (e.g., two uses), the medicated module may be locked out and prevented from further use. Thus, a medicated module in accordance with Applicants' proposed concept may be used with (i) a single drug delivery device for two injections or (ii) a first drug delivery device and a second new drug delivery device for two injections.

Specifically, in the first example, the single drug delivery device may be used to deliver a first dose that includes both the secondary medicament and the primary medicament, as well as a second dose that includes just the primary medicament. Further, in the second example, the medicated module may be used with a first drug delivery device to deliver a first dose that includes both the secondary medicament and the primary medicament, and the medicated module may then be used with a new (i.e., unused) second drug delivery device to deliver a dose that just includes the primary medicament. In either instance, after being used to deliver two doses, the medicated module locks out and is prevented from being used for a subsequent third delivery.

Figures 14A, 14B:
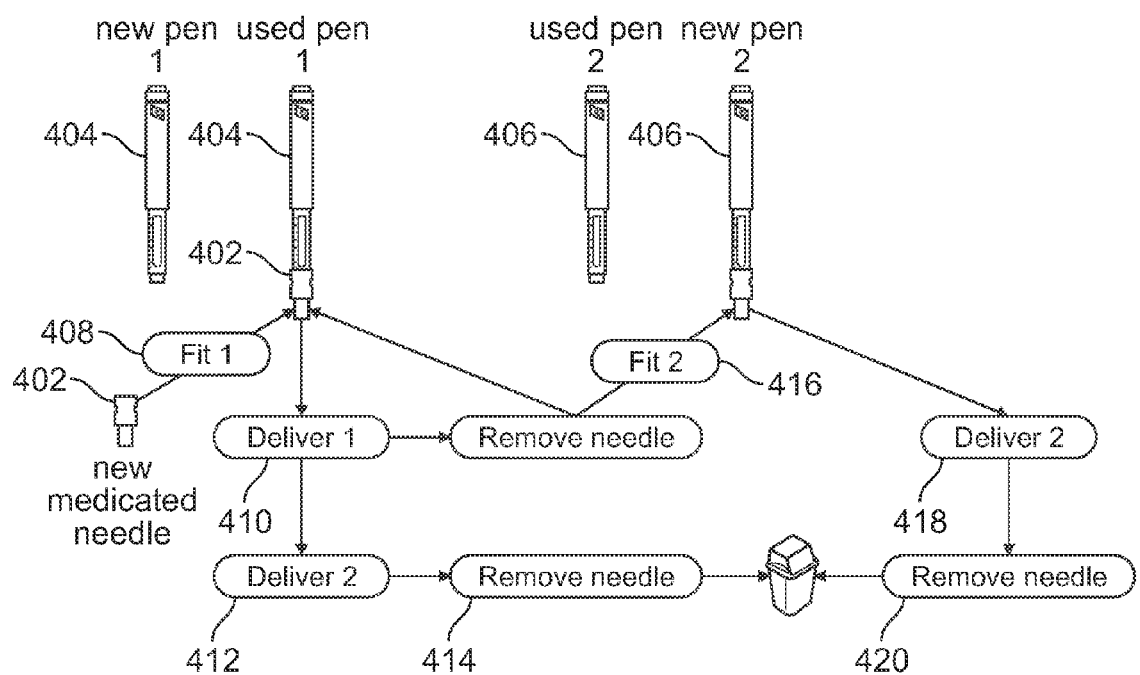

FIGS. 14a and 14b are figures that visually depict the split dosing scheme discussed above. In particular, FIG. 14a depicts a key 400 that illustrates the split dosing scheme of Applicants' proposed concept. As shown in key 400, a new medicated module may be used with either (i) a new drug delivery device (i.e., an unused drug delivery device) or (ii) a drug delivery device that has been used once at least once (a used device). In addition, as shown in key 400, a medicated module that has been used once may be used with a new drug delivery device. However, a medicated module that has been used once cannot be used with a drug delivery device that has been used once.

FIG. 14b is a flow chart that further clarifies this split dosing scheme shown in FIG. 14a and discussed above. FIG. 14b shows a medicated module 402, a first drug delivery device 404, and a second drug delivery device 406. At step 408, the new medicated module 402 may be connected to the first drug delivery device 404. At step 410, a user may deliver a first dose, which may comprise the primary medicament from the first drug delivery device and the secondary medicament from the medicated module 402. After step 410, a user may administer a split dose. In order to administer the split dose, the user may either (i) use the medicated module 402 to deliver a second dose from the first drug delivery device 404 or (ii) attach the medicated module 402 to a new or second drug delivery device 406. Alternatively, rather than administering a split dose, the user may simply dispose of the medicated module after step 410.

If the user chooses to use the medicated module 402 to deliver a second dose from the first drug delivery device 404, the user may deliver the second dose at step 412. Since the secondary medicament would have been expelled from the medicated module during the first dose of step 410, this second dose will be a dose of the primary medicament. As shown in FIG. 14b, a third delivery from this medicated module 402 is prevented (e.g., because the medicated module may be locked out). The medicated module will not be capable of being used with another drug delivery device. Therefore, the user may remove the medicated module at step 414 and then may dispose of the medicated module 402. The third delivery may be prevented in various ways, such as through a lock out feature in the medicated module that is triggered after two uses. Thus, the user may remove the medicated module 402 from the drug delivery device 404.

If the user, however, chooses to attach the medicated module to a new or second drug delivery device, the user may attach the medicated module 402 to drug delivery device 406 at step 416. The once-used medicated module 402 may be attached to a new (i.e., unused) drug delivery device, but cannot be attached to a drug delivery device that has been used one or more times. At step 418, the user may deliver a dose, which will be the second dose delivered with the medicated module 402. Since the secondary medicament would have been expelled from the medicated module during the first dose of step 410, this second dose will be a dose of the primary medicament contained within the drug delivery device 406. As shown in FIG. 14b, a third delivery from this medicated module is prevented. Therefore, the user may remove the medicated module at step 420 and then may dispose of the medicated module 402.

Figure 15:
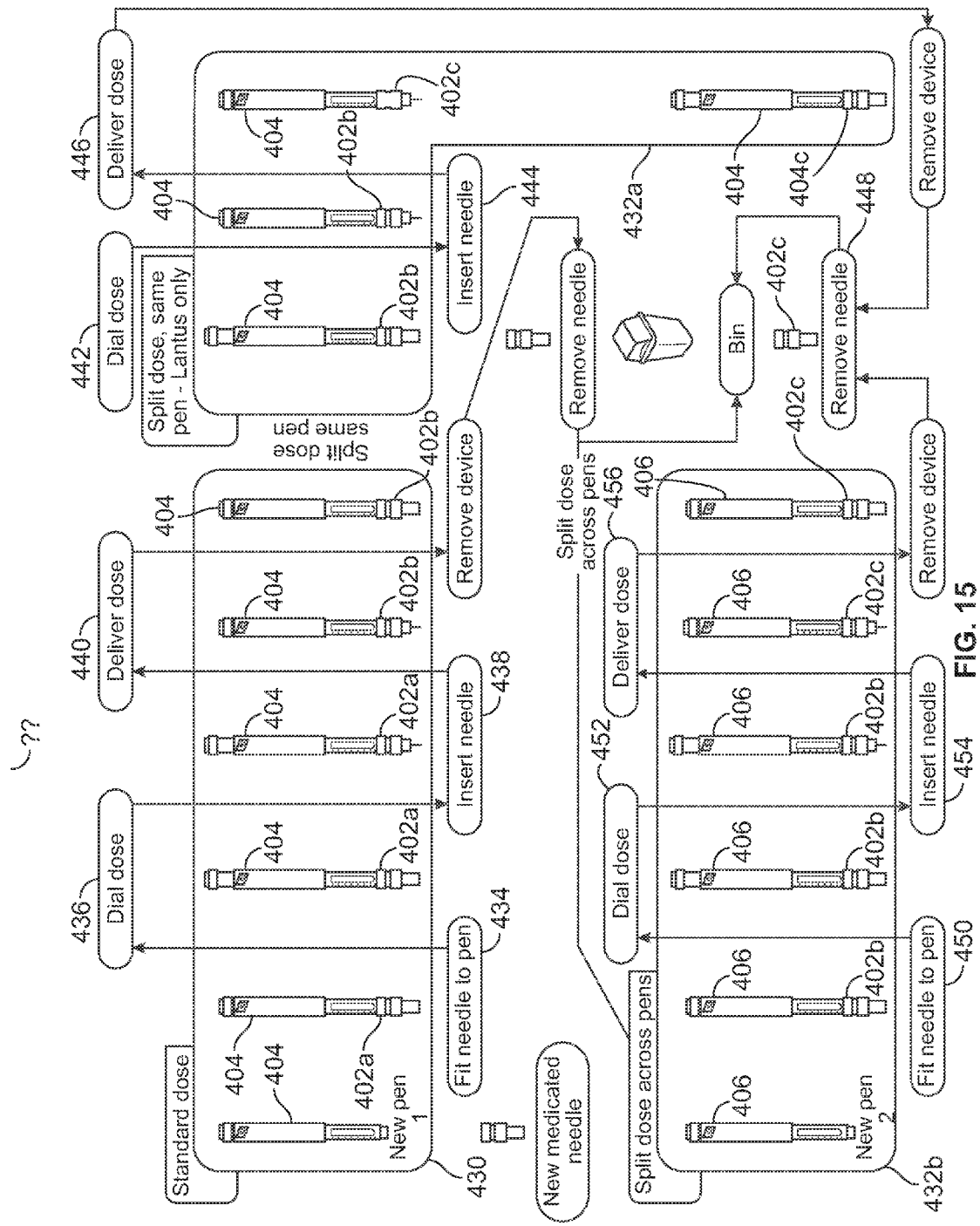

A more detailed logic flow chart of the example split dosing scheme is depicted in FIG. 15. This logic flow chart depicts three primary stages 430, 432a, and 432b. In a first split dosing scheme, a user may perform stages 430 and 432a. In a second split dosing scheme, the user may perform stages 430 and 432b. These are the stages described above with reference to FIG. 14b; however, the stages are described in slightly more detail with reference to FIG. 15. For clarity, although the same medicated module is depicted throughout the figure, the medicated module 402 is described as (i) medicated module 402a prior to being used, (ii) medicated module 402b after one use, and (iii) medicated module 402c after two uses.

Stage 430 comprises use of the medicated module 402 with drug delivery device 404 to deliver a first dose. A user may then use the medicated module 402 to deliver a second dose, and this may be delivered either with the same, once used drug delivery device 404 or a new, unused drug delivery device 406. Thus, after stage 430, a user may either proceed to stage 432a or stage 432b. In particular, stage 432a comprises use of the medicated module 402 with drug delivery device 404 to deliver a second dose. Further, stage 432b comprises use of the medicated module 402 with new, unused drug delivery device 406 to deliver a second dose.

In stage 430, a user may fit the medicated module 402a to the drug delivery device 404 at step 434. After the medicated module 402a is fitted to the drug delivery device 404, the drug delivery device state may be changed to "once used." The device state may be changed, for example, through mechanical logic. Particular examples of such mechanical logic will be discussed below. Generally, this state change may occur at any point between the fitting of the medicated module 402 to the drug delivery device to removal of the medicated module 402 from the drug delivery device.

Returning to FIG. 15, the user may then dial a dose at step 436. Next, the user may insert into an injection site the needle cannula of the medicated module 402a at step 438. During this step, a needle guard or cover of the medicated module may retract. At this point, the medicated module 402a is triggered to change its state to "used once" (e.g., through mechanical logic). As mentioned above, this "used once" state is depicted in FIG. 15 as medicated module 402b. In some examples, the medicated module state will change regardless of whether dose delivery has actually occurred, rather than just the retraction of the needle guard infers that it has been 'used' as intended. Additionally, in some examples, the medicated module 402 may comprise a visual indicator that shows that the medicated module has been used once. At step 440, a user may then deliver the first dose. This dose will include both the primary medicament from the drug delivery device and the secondary medicament from the medicated module.

As discussed above, the user may then either proceed to (i) administer a split dose using the same drug delivery device (i.e., stage 432a) or (ii) administer a split dose using a different drug delivery device (i.e., stage 432b). In stage 432a, the user may dial a second dose at step 442 and thereafter insert into an injection site the needle cannula of the medicated module 402b at step 444. Once again, during this step, a needle guard or cover of the medicated module may retract. At this point, the medicated module 402b is triggered to change its state to "used twice" (e.g., through mechanical logic). As mentioned above, this "used twice" state is depicted in FIG. 15 as medicated module 432c. In some examples, the medicated module may comprise a visual indicator that shows that the medicated module has been used twice. The user may then deliver the second dose at step 446. This second dose will include only the primary medicament from the drug delivery device since the secondary medicament was dispelled from the medicated module at step 440. After this second dose, the medicated module 402c may be locked out from further use, and the user may then remove the medicated module from drug delivery 404 and dispose of the medicated module 402c at step 448.

In stage 432b, at step 450 the user may attach the medicated module 402b to the new drug delivery device 406. After the medicated module 402b is fitted to the drug delivery device 406, the drug delivery device state may be changed to "once used" (e.g., through mechanical logic). This state change may occur at any point between the fitting of the medicated module 402*b* to removal of the medicated module 402*b*. The user may dial a second dose at step 452 and thereafter insert into an injection site the needle cannula of the medicated module 402*b* at step 454. Once again, during this step, a needle guard or cover of the medicated module may retract. At this point, the medicated module 402*b* is triggered to change its state to "used twice." As mentioned above, this "used twice" state is depicted in FIG. 15 as medicated module 432*c*. In some examples, the medicated module may comprise a visual indicator that shows that the medicated module has been used twice. The user may then deliver the second dose at step 456. This second dose will include only the primary medicament from the drug delivery device since the secondary medicament was dispelled from the medicated module at step 440. After this second dose, the medicated module 402*c* may be locked out from further use, and the user may then remove the medicated module from drug delivery 406 and dispose of the medicated module 402*c* at step 448.

Therefore, in Applicants' proposed system that facilitates safe split dosing, mechanical logic on the medicated module prevents the medicated module from being used for a drug delivery more than twice. Further, mechanical logic on a drug delivery device prevents a used drug delivery device from attaching to a used medicated module (but allows for a new drug delivery device to attach to a once-used medicated module).

In some examples, the drug delivery device and/or the medicated module may comprise visual indicators that serve to identify the status of the device or module (e.g., new, used-once, used-twice). For instance, a green visual indicator may serve to indicate that a medicated module is new, a yellow visual indicator may serve to indicate that the medicated module has been used once, and a red visual indicator may be used to indicate that the medicated module has been used twice.

In an embodiment, the mechanical means or logic assumes that a patient is forced to remove the medicated module from the drug delivery device after use in order to fit the protective over-cap on the drug delivery device. Beneficially, forcing the user to remove the needle from the device after use in order to fit the protective over-cap helps mitigate mono product use (either accidental or deliberate).

The interlock design described in reference to FIGS. 1-7 could be used in conjunction with an interlock feature present on a drug delivery device which is triggered on insertion, allowing fitment of a once-used medicated module to a new device (i.e., for a split dosing scenario).

As indicated, medicated modules and drug delivery devices may include mechanical logic that facilitates these safe, controlled split dosing schemes detailed above. Particular examples of such mechanical logic are shown in FIGS. 9-13 and 16. Other examples of different mechanical logic that facilitate safe, controlled split dosing are possible as well. One example of such mechanical logic is described with reference to FIGS. 9-11. In this example, both the drug delivery device (e.g., an injection pen) and the medicated module include torsionally sprung cylinders which rotate when triggered. Generally, in this example, the drug delivery device is triggered when a new medicated module is attached to the device. In some examples, the drug delivery device rotates as the medicated module is removed from the device, and this rotation serves to track that the drug delivery device has been used with a medicated module. Further, the medicated module is triggered a first time when the module is attached to the drug delivery device. The required/controlled fitting is due to the arrangement of the slot and lug positions of the device and module.

An example of Applicants' proposed mechanical logic is shown in FIG. 9. FIG. 9*a* depicts a cross-section of an unused (i.e., new) drug delivery device mechanical logic feature 200, while FIG. 9*b* depicts a cross-section of a used drug delivery device mechanical logic feature 201 (e.g., drug delivery device mechanical logic feature 200 that has been used once (i.e., attached and then removed from the medicated module)). FIG. 9*c* depicts a cross-section of an unused (i.e., new) medicated module mechanical logic feature 202, while FIG. 9*d* depicts a cross-section of a triggered medicated module mechanical logic feature 203 (i.e., medicated module 202 that has been used once (i.e., attached and then removed from the delivery device). In these examples, the medicated module may further include features that prevent the medicated logic from being used more than twice. For example, the medicated module may include a lock-out feature that locks the medicated module out after the module is used two times. This lock out feature may be separate from or integral with the described mechanical logic feature that tracks whether the medicated module has been attached to a drug delivery device.

With reference to FIG. 9*a*, drug delivery device mechanical logic feature 200 includes a fixed-alignment feature and a plurality of coded features, and medicated module mechanical logic feature 202 includes a corresponding fixed alignment feature and a plurality of coded features. The coded features of the drug delivery device mechanical logic feature and the coded features of the medicated module mechanical logic feature may be the inverse of one another. As such, the coded features may take any form. For instance, the coded features of the drug delivery device mechanical logic feature may comprise slots, while the coded features of the medicated module mechanical logic feature may comprise lugs. In this particular example, the drug delivery device mechanical logic feature 200 includes fixed alignment feature 204, slot 206, slot 208, and slot 210. The slots in this example are semi-circular indentations. However, other types of slots/defining features are possible as well. The medicated module mechanical logic feature 202 includes a corresponding fixed-alignment feature 212, lug 214, and lug 216. The alignment features on drug delivery device mechanical logic feature and medicated module mechanical logic feature have two primary functions. First, they may provide a primary location/alignment feature between the device and the medicated needle such that they could only go on a set way. Second, in conjunction with the first function, the alignment features are datums for the slot features/coded features so that they are correctly positioned and can consequently control the logic of the attachment system. The lugs are semi-circular protrusions that are complementary to the slots of the drug delivery device. These could be any design as long as they are an inverse of the feature on the device. These sets of features are designed as such to have sufficient geometry to prevent them attaching in incorrect orientations.

In this example, the medicated module mechanical logic feature 202 has one fewer lug than the drug delivery device mechanical logic feature 200 has slots. As will seen below, the position and difference in number of the lugs and slots provide the mechanical logic that prevents a used medicated module from being attached to a used drug delivery device, but allows a used medicated module to be attached to a new drug delivery device. It should be noted, however, in some examples, the medicated module mechanical logic feature and the drug delivery device mechanical logic feature could include the same number of lugs and slots, respectively. In such an example, the position of the respective slots and lugs could provide the mechanical logic that prevents a used medicated module from being attached to a used drug delivery device, but allows a used medicated module to be attached to a new drug delivery device.

With reference to X-Y axis 218 shown in FIG. 9*a*, when drug delivery device is unused, slot 206 is oriented at 90 degrees, slot 208 is oriented at 0 degrees, and slot 210 is oriented at 270 degrees. When medicated module mechanical logic feature 202 is unused, lug 214 is oriented at 90 degrees and lug 216 is oriented at 0 degrees. Thus, as indicated by arrow 220, the new medicated module mechanical logic feature 202 can be attached to the new drug delivery device mechanical logic feature 200. Due to the respective positions of the lugs and slots, when a user attempts to attach the drug delivery device mechanical logic feature 200 and medicated module mechanical logic feature 202, the lug features and slot features can mesh with one another to allow for attachment.

When the new medicated module mechanical logic feature 202 is attached to the new drug delivery device mechanical logic feature 200, the drug delivery device mechanical logic feature 200 is triggered. As mentioned above, both the drug delivery device and the medicated module include torsionally sprung cylinders attached/linked/integrated to the slot/lug features, which rotate after they have been triggered. Further, the medicated module mechanical logic feature 202 is triggered the first time it is inserted into drug delivery device mechanical logic feature 200 and the drug delivery device mechanical logic feature is triggered the first time a medicated module mechanical logic feature is attached to it. Example springs that act to torsionally spring the cylinders are depicted in FIG. 16.

Figure 16:
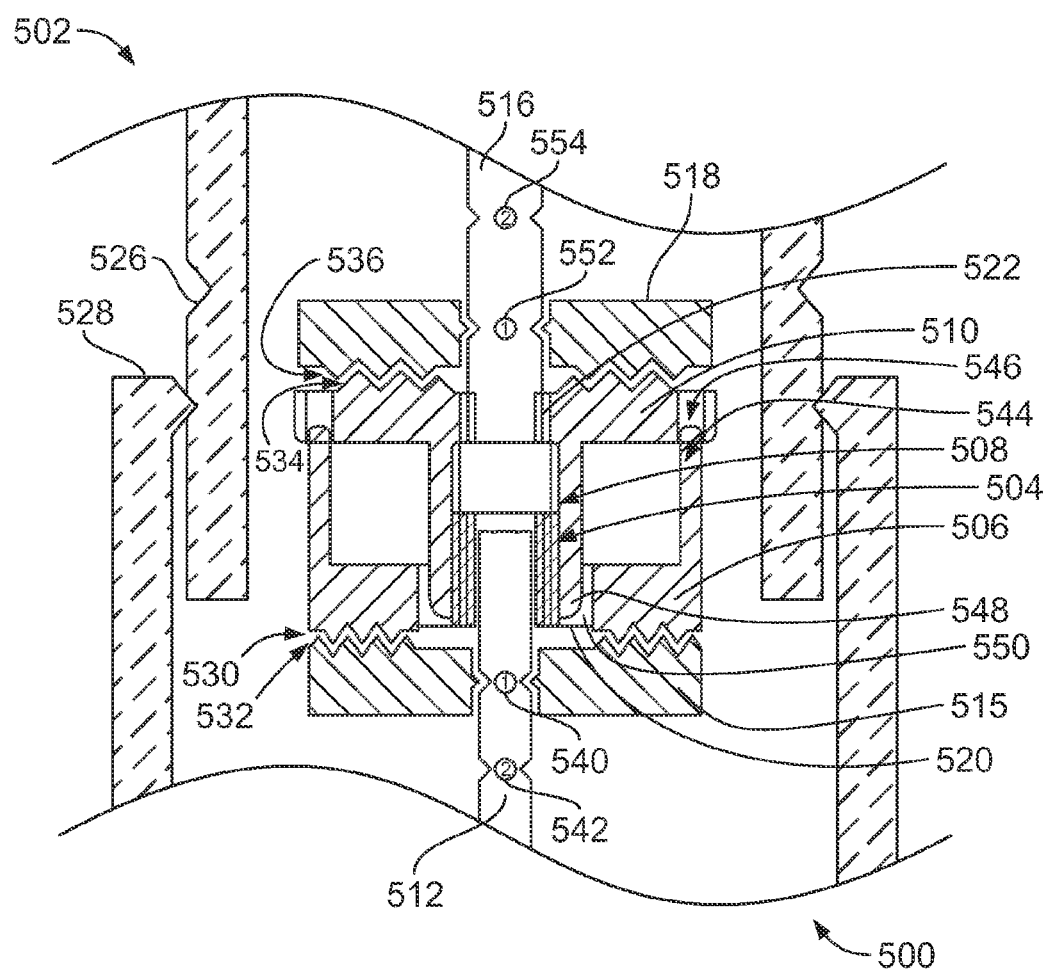
FIG. 16 is a cross-sectional view of an example medicated module and an example drug delivery device in a partially attached condition.

FIG. 16 shows a cross-section of an example medicated module 500 and an example drug delivery device 502 in a partially attached condition. Medicated module 500 and drug delivery device 502 may include mechanical logic features, similar to the mechanical logic features 200 and 202 of FIG. 9. In this example, medicated module 500 includes core element 506 that comprises mechanical logic feature 504. This core element 506 may be a cylindrical element that is capable of rotation. Further, drug delivery device 502 includes core element 510 that comprises mechanical logic feature 508. Similar to core element 506, the core element 510 may be a cylindrical element that is capable of rotation. These mechanical logic features 504, 508 take the form of cylindrical elements having splined slots and lugs that provide mechanical logic, similar to the mechanical logic features discussed about with reference to FIG. 9. In addition, the medicated module 500 also includes rod 512 and clutch plate 515. Drug delivery device 502 similarly includes rod 516 and clutch plate 518. The medicated module 500 may also include a torsion spring 520 that may be, for example, located between core element 506 and rod 512. Further, the drug delivery device may include a torsion spring 522 that may be, for example, located between core element 510 and rod 516. During use, these various features interact with one another in order to provide the mechanical logic discussed above with respect to FIGS. 14-15.

The outer connecting bodies of the medicated module and drug delivery device may be connected to one another using mutual attachment features, such as clip features 526 and 528. Although these attachment features are depicted as clip features, other attachment features are possible as well. Rotation of the core mechanism part 506 comprising mechanical logic feature 504 may occur under the action of the torsion spring 520 while rotation of core mechanism part 510 comprising mechanical logic feature 508 may occur under the action of the torsion spring 522.

In the medicated module 500, the core element 506 is temporarily prevented from rotating by clutch teeth 530 that are engaged with clutch teeth 532 on the clutch plate 515. Similarly, the core element 510 is temporarily prevented from rotating by clutch teeth 534 that are engaged with clutch teeth 536 on the clutch plate 518. Core element 506 is permanently axially constrained on a feature on rod 512, and core element 510 is permanently axially constrained on a feature on rod 516. Clutch plate 515 is permanently rotationally constrained and temporarily axially constrained in position 540. Further, clutch plate 518 is permanently rotationally constrained and temporarily axially constrained in position 552.

During attachment, the protruding proximal feature 544 of the core element 506 passes through a hole 546 of the core element 510. Similarly, a protruding distal feature 548 of the core element 510 passes through a hole 550 of the core element 506. During attachment, the protruding proximal feature 544 forces the clutch plate 518 from position 552 to position 554, and the protruding distal feature 548 forces the clutch plate 515 from position 540 to position 542. This displacement of the clutch plates is a permanent displacement. That is, the mechanical features of the medicated module and drug delivery device will not move the clutch plates from these final positions under normal operation.

Features C on cutch plate 518 interlocks core elements 506 and 510 such that only when the medicated module and device are being separated do core elements 506 and 510 rotate relative to their axis under the torsion load from the springs (this prevents a force 'battle' between springs once declutched, as one spring wants to rotate one way and the other the other way. The rotation is a permanent change in state such that the device and medicated module have registered the triggering/use. Features C are recesses in the clutch plate 518, which have two functions. Firstly they are the points where the protruding features (544,548) push against causing the clutch plates to move from one position to the next. Secondly, being a recess, although having moved the clutch plates, the protruding features are still engaged such that the core elements cannot rotate until the device and medicated module are separated. If these secondary anti rotation features were not present, the core elements would be trying to rotate against each other before the devices were separated. In basic terms it is analogous to placing a stick in someone's bike wheel while they try to pedal. Once the stick is removed, the wheel can turn. As such, in this instance the specific elements are prevented from rotating until the devices are separated. As discussed above with respect to FIG. 9, the rotation of the mechanical logic features of the drug delivery device provides an indication of the number of times the drug delivery device has been connected to a medicated module (or, more generally, an indication of whether the drug delivery device is new or used). In addition, the rotation of the mechanical features of the medicated module provides an indication of the number of times the medicated module has been attached to a drug delivery device (or, more generally, an indication of whether the medicated module is new or used). It should be appreciated from the above that rotation, yet axial constraint, of the core elements 506 and 510 means that both a new medicated module and a triggered/used medicated module could trigger a new/unused device.

Returning to FIG. 9, when drug delivery device mechanical logic feature 200 is triggered, the torsionally sprung cylinder rotates 90 degrees in the counterclockwise direction indicated by arrow 222. Thus, after drug delivery device is triggered, slot 206 is oriented at 180 degrees, slot 208 is oriented at 90 degrees, and slot 210 is oriented at 0 degrees. Further, when medicated module mechanical logic feature 202 is triggered, the torsionally sprung cylinder rotates 90 degrees in the clockwise direction indicated by arrow 224. Thus, after medicated module mechanical logic feature 202 is triggered, lug 214 is oriented at 0 degrees and lug 216 is oriented at 270 degrees. A perspective representative view of the coding features on a new medicated module mechanical logic feature 202 prior to attachment to new drug delivery device mechanical logic feature 200 is shown in FIG. 10.

As indicated by arrow 226, the new medicated module mechanical logic feature 202 can be attached to the triggered drug delivery device mechanical logic feature 201. Due to the respective positions of the lugs and slots and the fixed alignment features, the new medicated module mechanical logic feature 202 and the triggered drug delivery device 201 can mesh with one another. Further, as indicated by arrow 228, the triggered medicated module mechanical logic feature 203 can be attached to new drug delivery device mechanical logic feature 200. Due to the respective positions of the lugs and slots and the fixed alignment features, the triggered medicated module mechanical logic feature 203 and the new drug delivery device mechanical logic feature 200 can mesh with one another. However, the triggered medicated module mechanical logic feature 203 cannot be attached to the triggered drug delivery device mechanical logic feature 201. Due to the respective positions of the lugs and slots and the fixed alignment features, the triggered medicated module 203 cannot mesh with the triggered drug delivery device 201. Thus, the mechanical logic of the exemplary modules and devices of FIGS. 9-11 mechanically prevents a used medicated module from being used with a used drug delivery device Further, the exemplary modules of FIGS. 9-11 may be configured to prevent a twice-used medicated module from being used with either a new or used drug delivery device. As mentioned above, the medicated module may, for example, include a lockout feature that locks the medicated module out after two uses. Such a lock out mechanism could include a needle guard lock out mechanism that prevents a user from using the medicated module for more than two injections. A twice used medicated module could still be attached to a new pen (but not a used pen because of the mechanism explained in FIGS. 9-11) but the user would not be able to inject a dose as the needle guard would be locked in the extended position.

Figure 11:
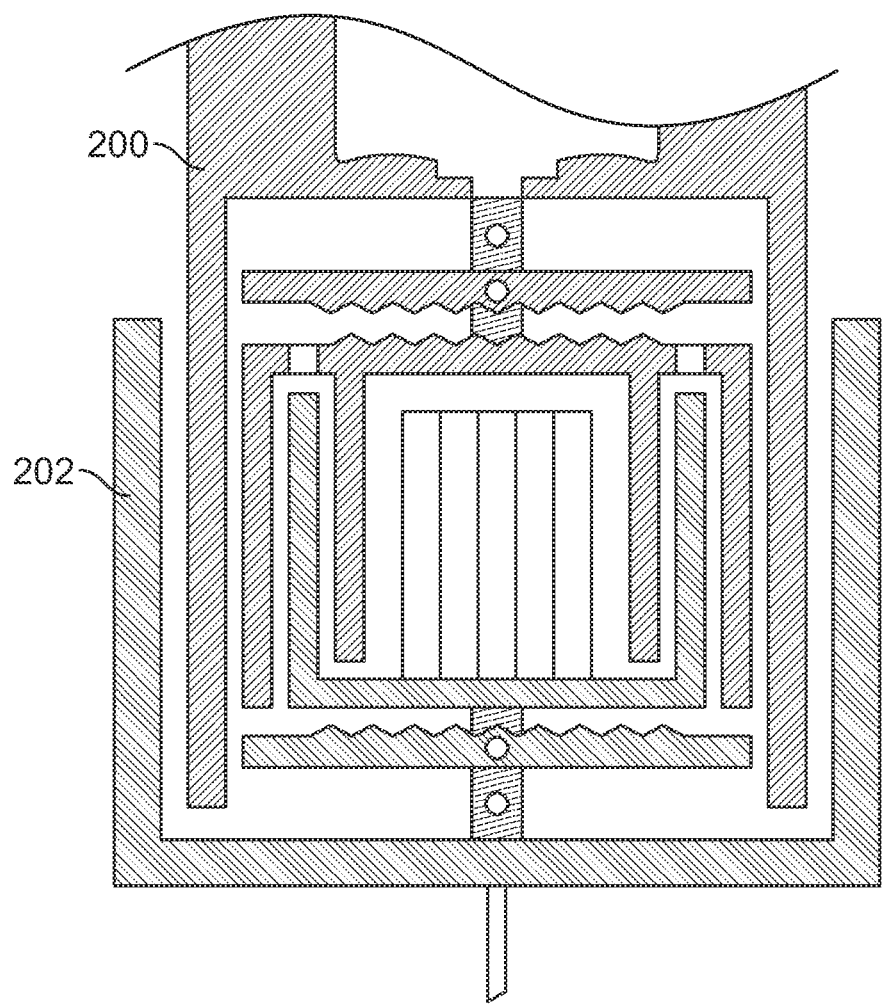
FIG. 11 depicts a cross-sectional view of an exemplary drug delivery device attached to an exemplary medicated module.

While FIGS. 9-11 depict that the drug delivery device includes a mechanical logic feature with slots and that the medicated module includes a mechanical logic feature with lugs, it should be understood that the opposite is also possible (i.e., the medicated module could include the slots while the drug delivery device includes the lugs). Further, the number of slots and lugs and the respective positions of the slots and lugs illustrated in FIGS. 9-10 is intended as an example only. It should be understood, that different numbers of slots and lugs are possible. Further, it should be understood that different positions of the slots and lugs are possible. Still further, it should be understood that the amount of rotation after the medicated module and/or drug delivery device are triggered may also vary in other examples (e.g., rotation of 10 degrees, 15, degrees, 45 degrees, 60 degrees, etc.).

Figure 12A:
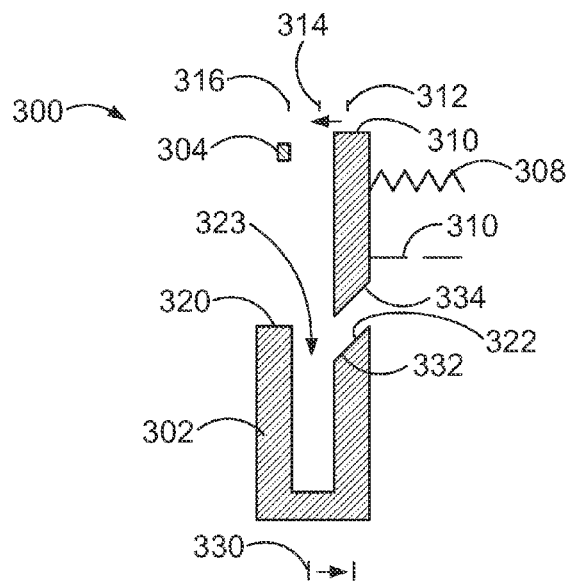
FIG. 12a depicts a cross-sectional view of an exemplary unused (i.e., new) medical delivery device and an exemplary unused medicated module.
Figure 12B:
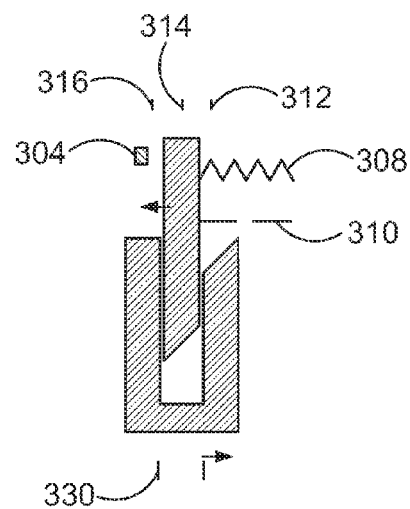
Figure 12C:
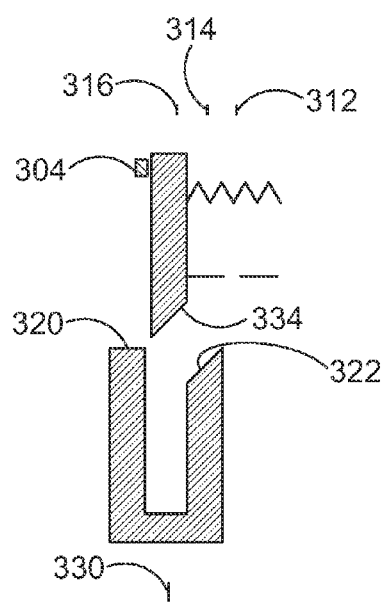
FIG. 12c depicts a cross-sectional view of the used medical delivery device of FIGS. 12a and b and an exemplary used medicated module.
Figure 12D:
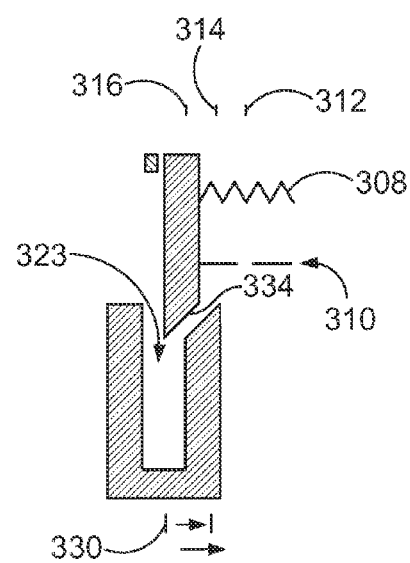
FIG. 12d depicts a cross-sectional view of a used medical delivery device being attached to an exemplary new medicated module.
Figure 13:
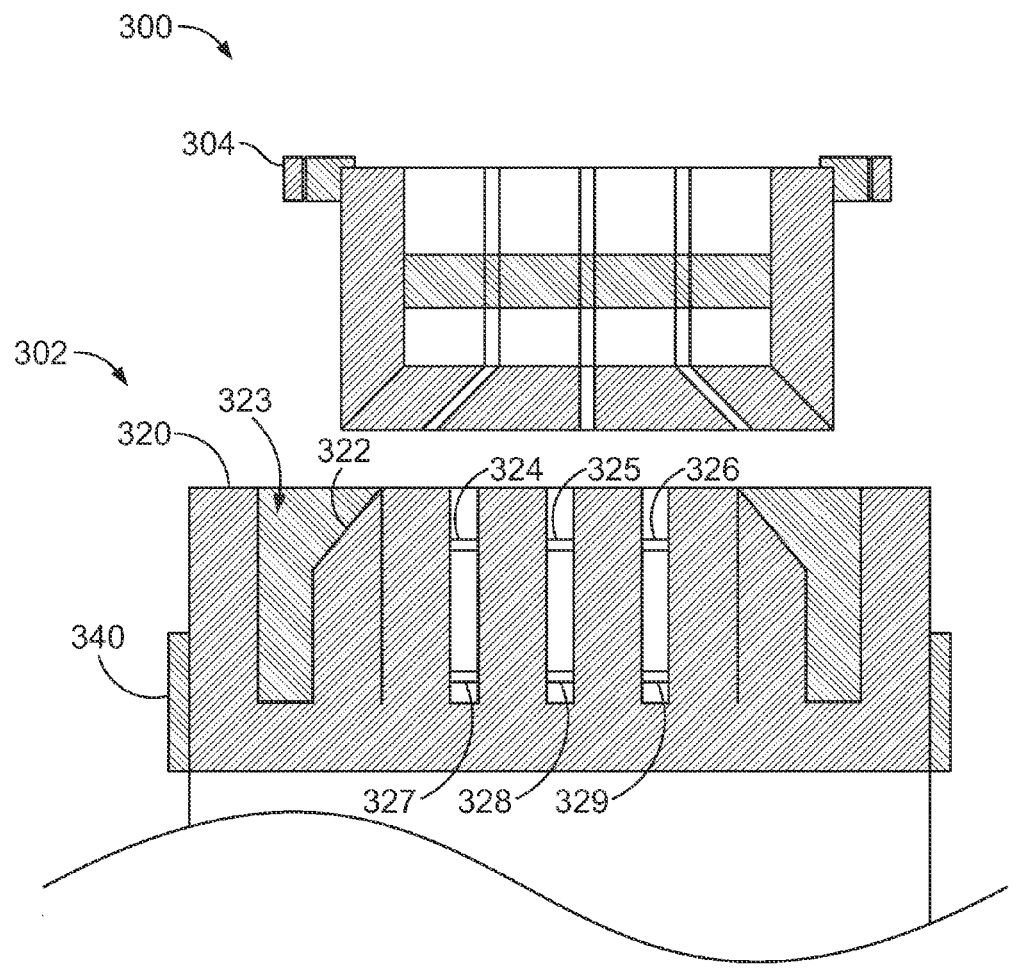
FIG. 13 depicts a cross-sectional view of a new medical delivery device being attached to an exemplary new medicated module.

Another example of Applicants' proposed mechanical logic is shown in FIGS. 12-13. Generally, in this example, both the drug delivery device and the medicated module have an annulus that is split into segments that are held closed and held open respectively. When triggered, the drug delivery device annulus is sprung outward and the medicated module annulus is sprung inward. Specifically, the drug delivery device annulus has three positions while the medicated module annulus has two positions. The drug delivery device positions include (i) a first, unsprung position, (ii) a second, sprung, but inserted position, and (iii) a third, sprung position (out of module). The medicated module positions include a new, unsprung position and a second, sprung position.

The body of the medicated module includes a chamfered section and a flat section. During the fitting of a new medicated module to a new drug delivery device, frangible elements on both the module and device fracture/break. This breaking allows the annulus diameters to grow or shrink into the second and third positions. The annuli are sized to give the correct fitting logic. As a result of the varying annuli, a new medicated module can be attached to a new drug delivery device and a used drug delivery device. However, a used medicated module can be attached to a new drug delivery device, but not a used drug delivery device.

FIGS. 12a-12d illustrate various positions of a medicated module and a drug delivery device in accordance with this example. Specifically, FIG. 12a illustrates new drug delivery device 300 prior to attachment to new medicated module 302. In FIG. 12a, the annulus of the drug delivery device is in its first position, and the annulus of the medicated module is in its first position. Drug delivery device 300 includes a stop feature 304. The device 300 also includes a body feature 306 that is connected to spring 308 and frangible element 310. As shown in FIG. 12a, the frangible element 310 is uniform. In other words, the frangible element is not yet broken. The frangible element may be a localized thin section of the same material as the main body of the annulus and is most likely to be integrated (i.e., molded) as part of the annulus. The material may be any injection moldable polymer.

Medicated module 302 includes a flat section 320 and a chamfered section 322. Indentation 323 is located between the flat section and the chamfered section. Further, as shown in FIG. 13, the medicated module 302 includes frangible elements 324-329. In this example, the module 302 includes six frangible elements. However, it should be understood that more or fewer frangible/extendable elements are possible.

The first, second, and third positions of the annulus of the drug delivery device will be described herein with reference to points 312, 314, and 316 respectively. Specifically, when the annulus is in the first position, the body feature is aligned with point 312, when the annulus is in the second position, the body feature is aligned with point 314, and when the annulus is in the third position, the body feature is aligned with point 316. It should be understood that the size of the annulus of the drug delivery device is dynamic (i.e., changing), depending on which position the annulus is in. Further, the position of the annulus depends on whether the drug delivery device has been used before. The positions of the annulus of the medicated module will be described herein with reference to point 330. When the annulus of the medicated module is in the first position, the indentation 323 is aligned with point 330. It should be understood, however, that these alignments as described and shown are intended as examples only. The various positions may be defined differently (e.g., by different elements aligning with different reference points).

Returning to FIG. 12a, the new drug delivery device 300 and new medicated module 302 (each having the respective annulus in the first position) may be attached to one another. When the module and device are attached, slanted surface 332 of the chamfered section 322 interacts with slanted surface 334 of the body feature of the drug delivery device. This interaction forces the frangible element 310 of the drug delivery device to break or extend. Thereafter, the spring 308 forces the body feature 306 to move outward in the radial direction. Meanwhile, the interaction of the module and device causes the frangible or retractable elements 324-329 of the module 302 to break or retract. Specifically, the interaction forces the chamfered section 322 to move inward, and this force effectively crushes the frangible elements 324-329. The annulus of the module, therefore, contracts. Further, sprung band 340 biases the medicated module to remain in this contracted second position.

FIG. 12b shows the drug delivery device when its annulus is in the second, extended position and the medicated module is in the second, contracted position. Specifically, the body feature 306 is aligned with reference point 314, and the flat section 320 is aligned with reference point 330. Notably, the spring does not force the body feature 306 into the third position, because, when the device is inserted into the module, the flat section 320 prevents the body feature 306 from springing out into the third position. In particular, the side of the flat section (i.e., the side of the recess) prevents the device feature moving any further. It is constrained by being within the recess.

When drug delivery device 300 is removed from the medicated module 302, the spring 308 forces the body feature 306 outward until the body feature is stopped from further radial movement by the stop feature 304. This is the third position, and the body feature 306 is aligned with reference point 316. FIG. 12c shows used drug delivery device 300 and used medicated module 302. As seen in the Figure, the used module and used device can no longer be attached to one another. If a user attempted to attach the two, the body feature would run into the flat section 320, and thus could not be inserted in indentation 323.

However, a new medicated module could be attached to the used drug delivery device 300. An example of this is shown in FIG. 12d and FIG. 13. Specifically, new medicated module 302 can be attached to used drug delivery device 300. As shown, the annulus of the used drug delivery device is in the third position, and the annulus of the new medicated module is in the first position. Specifically, indentation 323 is aligned with reference point 330. The slanted surface of the drug delivery device interacts with the slanted surface of the medicated module, in the same manners as described with reference to FIGS. 12a and 12b. Thus, the used device and new module may be attached to one another. Because the device feature is in its third position, when a new needle is attached, it will not move fully from position 1 to position 2 on insertion of the device into the recess. Only on removal of the device will the medicated module features move the remainder of the way (under the force of the sprung band) to a position as shown in FIG. 12c—thus preventing further attachment.

In the arrangements described herein, the second medicament may be either in a powdered solid state, any fluid state contained within the secondary reservoir or microcapsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

The shape of the medicated module may be a cylindrical body or any other geometric shape suitable for defining a fluid reservoir or for containing discrete self-contained reservoir of the secondary medicament and for attaching one or more needle cannula. The medicated module can be manufactured from glass or other drug contact suitable material. The integrated injection needle can be any needle cannula suitable for subcutaneous or intramuscular injection.

Preferably the medicated module is provided by a manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. This opening of the seal may be assisted by features such as angled surfaces on the end of the injection device or features inside the module.

The medicated module described herein should be designed to operate in conjunction with a multiple use injection device, preferably a pen-type multi-dose injection device, similar to what is illustrated in FIG. 8. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose, but in either case it is a multi-dose device.

A typical injection device contains a cartridge or other reservoir of medication. This cartridge is typically cylindrical in shape and is usually manufactured in glass. The cartridge is sealed at one end with a rubber bung and at the other end by a rubber septum. The injection pen is designed to deliver multiple injections. The delivery mechanism is typically powered by a manual action of the user, however, the injection mechanism may also be powered by other means such as a spring, compressed gas or electrical energy.

In certain embodiments where the medicated module contains a single dose of a medicament, the module is attached to a drug delivery device in order to administer the single dose in the reservoir to a patient. In other words, the medicated module cannot be used as a stand-alone injection device. This is because the module does not have a dose delivery mechanism and instead relies on the dose delivery mechanism contained in the drug delivery device to which it is attached.

Although Applicants' proposed mechanical logic is discussed primarily in regards to medicated modules, it should be understood that the mechanical logic may also apply to a standard needle or a safety needle type assembly. When applied to a standard needle assembly, the mechanical logic may prevent a user from re-using (by prevention of reattachment) a needle at all, once it has been taken off a device, or, it could prevent it being put back on the same device. In the latter situation the concept would be best integrated with a limited injection system such as a needle guard (i.e., a safety needle type assembly), otherwise a user could put the standard needle onto a new device and then use it multiple times.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module attachable to a drug delivery device, said medicated module comprising:
   a connecting body configured for attachment to said drug delivery device;
   a first needle fixed within a first needle hub of said connecting body;
   a second needle fixed within a second needle hub of said connecting body; and
   a recess within said connecting body defining a reservoir, said reservoir containing at least one dose of a medicament, said reservoir configured for fluid communication with said first needle,
   wherein said connecting body further comprises a lockout feature that prevents said medicated module from being reconnected to said drug delivery device after said medicated module has been connected to said drug delivery device a first time and subsequently removed, and
   wherein said lockout feature comprises a locking ring, said locking ring is rotated after said medicated module is attached to said drug delivery device so as to lock out said medicated module from being reconnected to said drug delivery device.

2. The medicated module of claim 1, further comprising:
   a needle guard operatively coupled to said connecting body; and
   a biasing element positioned between said connecting body and said needle guard.

3. The medicated module of claim 2, wherein when a dose of said medicament is injected by said medicated module, said needle guard moves in a proximal direction against a force created by said biasing element.

4. The medicated module of claim 2, wherein said needle guard is locked from moving in a proximal direction until said medicated module is connected to said drug delivery device.

5. The medicated module of claim 1, wherein when said medicated module is attached to said drug delivery device, said first needle pierces a drug delivery device reservoir.

6. The medicated module of claim 1, further comprising a bellows containing a priming fluid in fluid communication with a proximal end of said second needle.

7. The medicated module of claim 6, wherein said bellows is in fluid communication with a distal end of said first needle.

8. A drug delivery system comprising:
   a medicated module according to claim 1; and
   a drug delivery device comprising a dose setting mechanism, a reservoir holder coupled to the dose setting mechanism, wherein a distal end of the reservoir holder is configured for attaching the medicated module,
   wherein the system comprises a mechanical logic feature configured for (i) allowing a first use of the medicated module, (ii) allowing a subsequent use of the medicated module, wherein the second use occurs prior to the medicated module being detached from the drug delivery device, and (iii) preventing subsequent uses of the medicated module once removed.

9. The drug delivery system of claim 8, wherein the mechanical logic feature is further configured to, after allowing the use of the medicated module, prevent a subsequent use of a second medicated module different than the medicated module.

10. The drug delivery system of claim 9:
    wherein the mechanical logic feature is part of the drug delivery device,
    wherein the mechanical logic feature of the drug delivery device comprises (i) a fixed alignment feature and (ii) a plurality of coded features,
    wherein a corresponding mechanical logic feature of the medicated module comprises (i) a corresponding fixed alignment feature and (ii) at least one corresponding coded feature that corresponds to the each of the plurality of coded features of the mechanical logic feature of the drug delivery device, wherein the at least one corresponding coded feature is disposed on an outer wall of a core mechanism of the medicated module, and
    wherein the interaction of the plurality of coded features of the mechanical logic feature of the drug delivery device and the corresponding coding features serves to change a state of the drug delivery device from unused to used.

11. The drug delivery system of claim 8, wherein at least part of the mechanical logic feature is part of the drug delivery device.

* * * * *